(12) United States Patent
Ko et al.

(10) Patent No.: US 6,974,594 B2
(45) Date of Patent: Dec. 13, 2005

(54) METHOD OF PREPARING BIOLOGICAL MATERIALS AND PREPARATIONS PRODUCED USING SAME

(75) Inventors: Thomas S. Y. Ko, Montrose (AU); Terence P. Y. Au Yeung, Montrose (AU)

(73) Assignee: Gainful Plan Limited (VG)

(*) Notice: Subject to any disclaimer, the term of this patent is extended or adjusted under 35 U.S.C. 154(b) by 320 days.

(21) Appl. No.: 10/054,914

(22) Filed: Jan. 25, 2002

(65) Prior Publication Data

US 2003/0012819 A1 Jan. 16, 2003

(30) Foreign Application Priority Data

Jan. 25, 2001 (AU) .............................. PR2729

(51) Int. Cl.⁷ .......................... A61K 9/16; A61K 9/20; A61K 9/22; A61F 2/00
(52) U.S. Cl. ...................... 424/493; 424/422; 424/423; 424/427; 424/434; 424/435; 424/439; 424/440; 424/464; 424/468; 424/490; 514/772.3; 514/774; 514/776; 514/777; 514/778; 514/779; 514/782
(58) Field of Search .................... 424/422, 427, 424/434, 435, 423, 464, 439, 468, 490, 493, 440, 494

(56) References Cited

U.S. PATENT DOCUMENTS 6,596,318 B2 * 7/2003 Prasch et al. ............... 424/499

FOREIGN PATENT DOCUMENTS

| AU | 78721/87 | 3/1988 |
| AU | 23673/92 | 2/1993 |

OTHER PUBLICATIONS

Cleland et al, *Pharm. Res.*, 13(10):1464–1475 (1996), Abstract.
Cleland et al, *Pharm. Res.*, 14(4):420–425 (1997), Abstract.
Yang et al, *J. Pharm. Sci.*, 86(8): 908–914 (1986), Abstract.
Johnson et al, *Pharm. Res.*, 14(6):730–735 (1997), Abstract.
Jones et al, *Adv. Drug Deliv. Rev.*, 28(1):71–84 (1997), Abstract.
Kim et al, *Biotechnol. Bioeng.*, 65(6):659–667 (1999), Abstract.
Carrasquillo et al, *J. Pharm. Sci.*, 88(2):166–173 (1999), Abstract.
Blanco et al, *Eur. J. Pharm. Biopharm.*, 45(3):285–294 (1998), Abstract.
Constantino et al, *J. Pharm. Sci.*, 87(11):1412–1420 (1998), Abstract.
Johnson et al, *Nat. Med.*, 2(7):795–799 (1996), Abstract.
Brodbeck et al, *Pharm. Res.*, 16(12):1825–1829 (1999), Abstract.

(Continued)

*Primary Examiner*—James M. Spear
(74) *Attorney, Agent, or Firm*—Sughrue Mion, PLLC

(57) ABSTRACT

Methods for preparing products containing moisture-sensitive materials, including biological materials such as proteins, peptides or live cells, comprising at least the steps: (i) providing a coating liquid comprising at least one active, a sugar polymer and a water soluble/miscible solvent; (ii) providing a quantity of microparticles comprising at least water soluble gel forming solid particles; (iii) fluidizing said quantity of microparticles within a processing chamber of a of a suitable apparatus to form a fluidized bed of said microparticles; (iv) spraying said coating liquid onto said fluidized bed from beneath the fluidized bed to coat said microparticles therewith under saturated moisture conditions; and (vi) allowing coated microparticles to dry, are described. Also described are compositions and uses.

11 Claims, 1 Drawing Sheet

OTHER PUBLICATIONS

Figure 1:
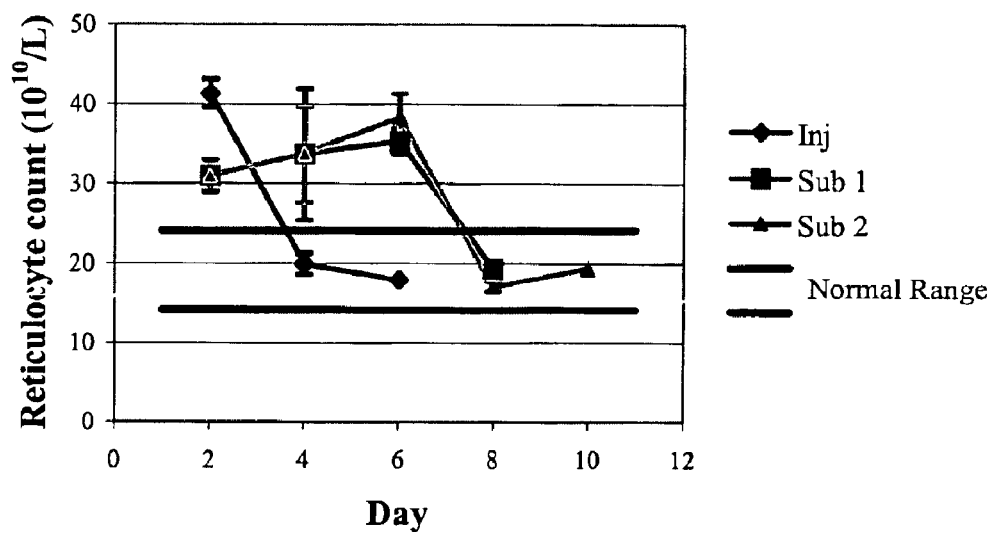

Sah et al, *PDA J. Pharm. Sci. Technol.*, 53(1):3–10 (1999), Abstract.
Park et al, *J. Controlled Release*, 55(2–3):181–191 (1988), Abstract.
Schwendeman et al, *J. Microencapsul.*, 15(3):299–318 (1998), Abstract.
Gupta et al, *Vaccine*, 15(6–7):672–678 (1997), Abstract.
Chang et al, *J. Pharm. Sci.*, 85(2):129–132 (1996), Abstract.
Alonso et al, *Pharm. Res.*, 10(7):945–953 (1993), Abstract.
Maa et al, *J. Pharm. Sci.*, 87(2):152–159 (1998), Abstract.
Shenderova et al, *Pharm. Res.*, 14(10):1406–1414 (1997), Abstract.
Uchida et al, *J. Microencapsul.*, 13(5):509–518 (1996), Abstract.
Uchida et al, *Chem. Pharm. Bull*, 44(1):235–236 (1996), Abstract.
Lu et al, *PDA J. Pharm. Sci., Technol.*, 49(1):13–19 (1995), Abstract.
Cohen et al, *Pharm. Res.*, 8(6):713–720 (1991), Abstract.
Lam et al, *J. Controlled Release*, 67(2–3):281–292 (2000), Abstract.
Jain et al, *J. Microencapsul.*, 17(3):343–362 (2000), Abstract.
Tracy, *Biotechnol. Prog.*, 14(1):108–115 (1998), Abstract.
Tzannis et al, *J. Pharm. Sci.*, 88(3):351–359 (1999), Abstract.
Katakam et al, *Pharm. Dev. Technol.*, 2(2):143–149 (1997), Abstract.
Schwendeman et al, *Dev. Biol. Stand.*, 87:293–306 (1996), Abstract.
Cleland, *Pharm. Biotechnol.*, 10:1–43 (1997), Abstract.
Okada et al, *Crit. Rev. Ther. Drug Carrier Syst.*, 12(1):1–99 (1995), Abstract.
Alonso et al, *Vaccine*, 12(4):299–306 (1994), Abstract.
Leo et al, *J. Microcapsul.*, 15(4):421–430 (1998), Abstract.
Putney, *Curr. Opin. Chem. Biol.*, 2(4):548–552 (1998), Abstract.
Lam et al, *Pharm. Res.*, 14(6):725–729 (1997), Abstract.
Takada et al, *PDA J. Pharm. Sci. Technol.*, 49(4):180–184 (1995), Abstract.
Sato et al, *Pharm. Res.*, 5(1):21–30 (1988), Abstract.
Pikal et al, *Pharm. Res.*, 8(4):427–436 (1991), Abstract.
Costantino et al, *J. Pharm. Sci.*, 87(11):1406–1411 (1988), Abstract.
Torres et al, *J. Microencapsul.*, 13(1):41–51 (1996), Abstract.
Prestrelski et al, *Arch Biochem. Biophys.*, 303(2):465–473 (1993), Abstract.
Hellebust et al, *Biotechnol Appl. Biochem.*, 18(Pt 3):227–237 (1993), Abstract.
Zhu et al, *Pharm. Res.*, 17(3):351–357 (2000), Abstract.
Maa et al, *Pharm. Dev. Technol.*, 2(3):213–223 (1997), Abstract.
Zhang et al, *Pharm. Res.*, 12(10):1447–1452 (1995), Abstract.
Iwata et al, *Pharm. Res.*, 10(8):1219–1227 (1993), Abstract.
Heya et al, *J. Pharm. Sci.*, 83(5):636–640 (1994), Abstract.
Mumenthaler et al, *Pharm. Res.*, 11(1):12–20 (1994), Abstract.
Maharaj et al, *J. Pharm. Res.*, 73(1):39–42 (1984), Abstract.
Alex et al, *J. Microencapsul.*, 7(3):347–355 (1990), Abstract.
Kendrick et al, *Proc. Natl. Acad. Sci. USA*, 95(24):14142–14146 (1998), Abstract.
Uchida et al, *J. Pharm. Pharmacol.*, 47(7):556–560 (1995), Abstract.
Sanghvi et al, *J. Microencapsul.*, 10(2):181–194 (1993), Abstract.
Arakawa et al, *Biopolymers*, 29(6–7):1065–1068 (1990), Abstract.
Johansen et al, *Eur. J. Pharm. Biopharm.*, 47(3):193–201 (1999), Abstract.
Pikal et al, *Dev. Biol. Stand.*, 74:21–37 (1992), Abstract.
Tzannis et al, *J. Pharm. Sci.*, 88(3):360–370 (1999), Abstract.
Uchida et al, *J. Microencapsul.*, 13(2): 219–228 (1996), Abstract.
Tabata et al, *Pharm. Res.*, 10(4):487–496 (1993), Abstract.
Gander et al, *J. Microencapsul.*, 12(1):83–97 (1995), Abstract.
Hora et al, *Pharm. Res.*, 7(11):1190–1194 (1990), Abstract.
Oroszlan et al, *Anal. Chem.*, 64(14):1623–1631 (1992), Abstract.
Green et al, *Toxico. Lett.*, 64–65:Spec. No. 321–327 (1992), Abstract.
Pavlu et al, *Bioseparation*, 3(5):257–265 (1992–1993), Abstract.
Andya et al, *Pharm. Res.*, 16(3):350–358 (1999), Abstract.
Hayes et al, *Biotechnol. Bioeng.*, 59:557–566 (1998), Abstract.
Eyles et al, *J. Pharm. Pharmacol.*, 49(7):669–674 (1997), Abstract.
Heelan et al, *J. Microencapsul.*, 14(1):63–78 (1997), Abstract.
Di Silvio et al, *Biomaterials*, 15(11):931–936 (1994), Abstract.
Arakawa et al, *Biochemistry*, 29(7):1914–1923 (1990), Abstract.
Wan et al, *J. Microencapsul.*, 9(3):309–316 (1992), Abstract.
Bam et al, *J. Pharm. Sci.*, 87(12):1554–1559 (1998), Abstract.
Leuckel et al, *Pharm. Dev. Technol.*, 3(3):337–346 (1998), Abstract.
Carpenter et al, *Arch Biochem. Biophys.*, 303(2):456–464 (1993), Abstract.
Pongpaibul et al, *J. Pharm. Pharmacol.*, 40(8):530–533 (1988), Abstract.
Iwata et al, *J. Microencapsul.*, 9(2):201–214 (1992), Abstract.
Vudathala et al, *Pharm. Res.*, 9(6):759–763 (1992), Abstract.
Huatan et al, *J. Microencapsul.*, 12(5):557–567 (1995), Abstract.
Chen et al, *J. Microencapsul.*, 11(4):395–407 (1994), Abstract.
Uchida et al, *Biol. Pharm. Bull.*, 17(9):1272–1276 (1994), Abstract.
Short et al, *Pharm. Res.*, 12(8):1140–1145 (1995), Abstract.
Margalit et al, *J. Microencapsul.*, 2(3):183–196 (1985), Abstract.
Jones et al, *J. Pharm. Pharmacol.*, 41(12):813–816 (1989), Abstract.
Costantino et al, *Biotechnology*, 13(5):493–496 (1995), Abstract.
Ma et al, *J. Drug Target*, 2(1):9–21 (1994), Abstract.
Bindschaedler et al, *J. Pharm. Sci.*, 77(8):696–698 (1988), Abstract.

Page et al., *J. Pharm. Pharmacol.*, 52(1):19–26 (2000), Abstract.

Duddu et al, *Pharm. Res.*, 14(5):591–595 (1997), Abstract.

Anchordoquy et al, *Arch. Biochem., Biophys.*, 332(2):231–238 (1996), Abstract.

Sah et al, *Pharm. Res.*, 13(3):360–367 (1996), Abstract.

Tsai et al, *Pharm. Res.*, 10(5):649–659 (1993), Abstract.

Gekko et al, *Biochemistry*, 20(16):4667–4776 (1981), Abstract.

Tabata et al, *Pharm. Res.*, 6(5):422–427 (1989), Abstract.

Kita et al, *Drug. Des. Deliv.*, 6(3):157–167 (1990), Abstract.

Hora et al, *Pharm. Res.*, 9(1):33–36 (1992), Abstract.

Costantino et al, *J. Pharm. Sci.*, 86(12):1390–1393 (1997), Abstract.

Cedrati et al, *Artif. Cells Blood Substit. Immobil. Biotechnol.*, 22(3):867–873 (1994), Abstract.

Weiner et al., *Immunomethods*, 4(3):201–209 (1994), Abstract.

Sah et al, *J. Microencapsul.*, 12(1):59–69 (1995), Abstract.

Shukla et al, *Pharm. Res.*, 6(5):418–421 (1989), Abstract.

Watts et al, *Crit. Rev. Ther. Drug Carrier Syst.*, 7(3):235–239 (1990), Abstract.

Yoshioka et al, *J. Pharm. Sci.*, 87(2):147–151 (1998), Abstract.

Charman et al, *Pharm. Res.*, 10(7):954–962 (1993), Abstract.

Knepp et al, *Pharm. Res.*, 15(7):1090–1095 (1998), Abstract.

Charman et al, *J. Pharm. Sci..*, 89:168–177 (2000).

McLennan et al, "Molecular Weight is a Primary Determinant for Lymphatic Absorption of Proteins Folowing Subcutaneous Administration", Podium Session 4, Paper 5, *Proceedings of the Australasian Pharmaceutical Science Association*Annual Conference 2001.

Porter et al, *Adv. Drug Del. Rev.*, 50:157–171 (2001).

Porter et al, *J. Pharm. Sci.*, 89(3):297–310 (2000).

* cited by examiner

METHOD OF PREPARING BIOLOGICAL MATERIALS AND PREPARATIONS PRODUCED USING SAME

FIELD

The present invention generally relates to a method of preparing biological materials, and particularly, but not exclusively, to a method of preparing biological proteins.

BACKGROUND

Many biological materials, such as proteins or whole cells, which may be useful in treatment and prevention of human and animal diseases or as food supplements, for example, are known to have a limited shelf life. This limitation is generally considered to be a result of protein instability at storage temperature, for example room temperature. The shelf life of certain proteins, and/or, cell cultures, may be extended by storing them at refrigeration temperatures (that is, 4° C. to 8° C.), however, even at such temperatures a shelf life of less than eighteen months is common.

As will be appreciated, biologically active proteins are generally folded in a complex three dimensional manner which is unique to each protein. The proteins are generally organised on three levels; having a primary structure, consisting of a linear chain of covalently bonded amino acid residues (a peptide chain); a secondary structure, in which the peptide chain folds into regular patterns (such as, α helices and β-pleated sheets); and a tertiary structure in which the folded chain further folds upon itself to form a compact structure. In addition, some proteins consist of more than one polypeptide chain held in close arrangement to form what is referred to as the quaternary structure. It is the tertiary and/or the quaternary structure which dictates a proteins ultimate biological activity.

The ultimate structure of a protein may be affected by a number of environmental factors; for example, temperature, pH, the presence or absence of certain co-factors or metals, presence of oxygen, enzymes, oxidising or reducing agents and the presence of water or moisture. Where conditions are not optimal, a protein may not form properly or may denature, such that its biological function is lost, or is at least diminished.

The cells of animals, plants and microorganisms may be considered complex protein materials in the broadest sense as they contain numerous proteins enclosed by a cell membrane and/or cell wall, which membrane or wall inturn presents additional proteins at the cell's surface. As with proteins, the viability of a cell is dependent on the environment in which it resides; for example, temperature, pH, the presence or absence of certain co-factors or metals, presence or absence of certain nutrients, metabolic waste, oxygen, enzymes, oxidising or reducing agents and the presence of water or degree of moisture may individually or collectively act to effect viability. As an example, the bacteria *Lactobacilli* and *Bifidus*, which are of commercial significance due to their common usage in yogurt or as a probiotic in human or animal health nutritional products, generally can survive at 4° C. for only a short period of time. At temperatures elevated above 4° C., or during heat/freeze-drying, for example, such bacteria die due to dehydration. The main cause of the death of the bacterial cells is thought to be attributed to the denaturation of the proteins residing within the cell and at the cells surface.

Cell cultures (including bacterial cell cultures) and biological proteins are normally made in solution. However, water is known to hydrolyse protein in a time and temperature dependent manner resulting in denaturation and potential loss of function. Dehydrating such cultures or protein solutions may not improve their stability as during dehydration, and at the high temperatures at which known dehydration procedures may occur, the proteins may also be denatured. Refrigeration of cell cultures and proteinaceous solutions, or the freeze-drying thereof, has been used in an attempt to curb such problems.

Freeze-drying under vacuum (lyophilization) is commonly used in industry to prepare proteins for use in vaccines and the like. The process traditionally involves freezing a solution of the biological protein removing ice crystals therefrom by converting them into water vapour under vacuum (sublimation). Unfortunately, this process can cause damage to the native structure of the protein.

To help increase the stability of a biological protein being prepared by freeze-drying, additives such as buffering or stabilising agents may be used in the product formulation. However, during freeze-drying, when the temperature of the solution is slowly reduced to minus 20° C. over a period of days, the additives may solidify at different freezing points. As a result, the end product may be a fine puffy cake-like substance actually made up of different layers, each representing an individual component. In essence, the additives added to protect the biological protein may be physically and chemically separated therefrom rendering them useless as protective agents.

An alternative procedure, which is commonly used in the food and dairy industry, to make dry fruit concentrates and milk powders, for example, is spray-drying-using-heat. This process involves spraying a fine mist of solution downwards from the top of a spray tower against an upward current of hot air. The hot air removes water from the droplets before they reach the bottom of the tower. Spray drying normally operates at an inlet air temperature exceeding 190° C. and the product temperature may well exceed 60° C. At this operating environment, most of the biological protein or cells, such as bacterial cells, denature.

Another protein preparation process known in the art is supercritical fluid drying. In this process, biological agents such as peptides, proteins and nucleic acids are maintained in an aqueous solution until particle formation. The aqueous solvent is removed at the time of particle formation using controlled hydrogen-bonding solvents, such as ethanol, acetone, and isopropanol in carbon dioxide above the critical point of the supercritical fluid solvent mixture.

Fluid bed spray drying is a modified spray-drying-using-heat technology. The process is commonly used in the pharmaceutical and chemical industry for tablet granulation and/or for drying heat stable materials. The process involves spraying a fine mist of solution containing actives downward from the top of a spray head towards a mass of dry excipients. Simultaneously, an upward current of hot air is passed through the mass of excipients to create a fluidized bed. The hot air removes water from the fluidized wet solids at the bottom of the fluid bed.

Fluid bed spray drying technology may be applicable to pharmaceutical proteins which are heat stable around 50° C. to 60° C. However, the native structure of the protein may be compromised and accordingly the protein may loose all, or at least some, of its biological activity.

Further problems may be associated with fluid bed spray drying as described above; for example, the spray nozzles, which are positioned near the top of the processing chamber, are required to have substantial clearance above the surface of the fluidized bed of excipient materials so that the such materials do not block the spraying nozzles; a substantial amount of the coating material, or liquid containing the active ingredient(s), may block the nozzles' filter system leading to processing loss; and such top spraying fluid bed operation may only be ideal for granulation rather than for spray coating purposes.

Fluid bed spray drying apparatus have been designed which spray liquid containing the active ingredient(s) from the bottom of the processing chamber. For example, the Roto-processor™ (Aeromatic, Switzerland) designed for pellet coating (pellets of approximately 1 mm or above in diameter), and the Aerocoater™ processor (Aeromatic, Switzerland) designed for coating kernels, granules, pellets and small tablets. It is considered that neither the Roto-processor™ nor the Aerocoater™ are designed for microparticle coating.

Of the techniques available, prior to the development of the present invention, for preparing biological proteins and cells, the technique of microencapsulation may be considered the most useful. Typically, no major equipment is required and the batch size can be as small as 10 g to 20 g thus making it useful for the preparation of biological proteins that may not be plentiful. This process uses organic solvents to solubilize the biological protein which is then encapsulated in polymeric microspheres using either a water-in-oil-in-water (w/o/w) or a solid-in-oil-in-water (s/o/w) emulsion method. Protein is captured into the solid microspheres after water is removed by simple filtration and the solvent is evaporated off.

Microencapsulation technology has been used to make carbon or self-adhesive paper in the paper industry and at least in Japan, food products, such as artificial fish eggs and decorative products are made using gelatin microcapsules to entrap fish or meat flavours.

While microencapsulation may be considered a favourable means to prepare biological proteins and whole cells for storage and future use, the technology is still at the developmental stage in the pharmaceutical and biotechnological industries. The technology has apparent difficulties in that proteins are likely to be denatured by the solvents used and by the necessary emulsifying/homogenising process. In addition, the quality of a product produced according to this process, may be considered undesirable due to the fact that traces of solvent remain in the core of the microcapsules; the traces of such solvents may hamper the commercialisation of a product produced using this technology.

If biologically active proteins and viable cell cultures could be prepared such that they were substantially stable at room temperature, it may increase their shelf life and obviate the need for refrigeration. At the same time, various alternative drug delivery methods could be explored, such as conventional oral delivery, sublingual delivery, nasal delivery, buccal delivery, occal and even dermal delivery. Such alternative administration methods may minimize the invasive nature of the commonly used injection delivery, and create vast commercial opportunities to fully explore the use of all these molecules.

Bibliographic details of the publications referred to herein are collected at the end of the description.

OBJECT

It is an object of the present invention to provide an improved method of preparing biological materials, and biological materials produced therefrom, or at least to provide the public with a useful choice.

STATEMENT OF INVENTION

In one broad aspect of the present invention there is provided a method of preparing products containing moisture-sensitive materials, including biological materials such as proteins, peptides or live cells, comprising at least the steps:
i) providing a coating liquid comprising at least one active, a sugar polymer and a water soluble/miscible solvent;
ii) providing a quantity of microparticles comprising at least water soluble gel forming solid particles;
iii) fluidizing said quantity of microparticles within a processing chamber of a suitable apparatus to form a fluidized bed of said microparticles;
iv) spraying said coating liquid onto said fluidized bed from beneath the fluidized bed to coat said microparticles therewith under saturated moisture conditions; and
v) allowing coated microparticles to dry.

The process of the invention may further comprise one or more additional coating steps which further coat the microparticles with an enteric coating, a film coating, a moisture repellant coating or taste masking coating.

Preferably the coated microparticles are heat dried.

Preferably, said active comprises proteins, peptides, or cells.

The coating liquid of the present invention preferably comprises additional constituents such as amino acids, proteins, chelating agents, buffers, preservatives, stabilizers, antioxidants, lubricants and other additives which may act to compliment the function of, or stabilize, the active contained therein.

Preferably said water soluble/miscible solvent is either or both of glycerol or propylene glycol.

Preferably said sugar polymer is selected from one of the following: dextran, fructose, fruitose, glucose, invert sugar, lactitol, lactose, maltitol, maltodextrin, maltose, mannitol, sorbitol, sucrose, trehalose, isomalt, xylitol, polydextrose; or combination thereof.

Preferably said water soluble gel forming solid particles comprise at least one or more of the following; acrylate and derivatives, albumin, alginates, carbomers, carrageenan, cellulose and derivatives, dextran, dextrin, gelatin, polyvinylpyrrolidone, and starch.

Preferably binding agents selected from one of the following polymers of acrylate and derivatives, albumin, alginates, carbomers, carrageenan, cellulose and derivatives, dextran, dextrin, gelatin, polyvinylpyrrolidone, starch or combination thereof.

Preferably the process is conducted in a Huttlin Turbojet™ Coater.

Preferably the product processing weight exceeds 50% w/v of the fluid bed processing chamber. More preferably the processing weight exceeds 75% w/v.

Preferably the process is conducted in a moisture saturated environment.

Preferably the process is conducted within the processing chamber of the apparatus in an enclosed sterile environment.

Preferably the process is conducted in an oxygen-free environment. In such case, the air within the processing chamber may be replaced by nitrogen, or another suitable inert gas.

A room temperature stable product produced according to the method herein described.

Preferably, said product contains at least one of a protein, peptide or a cell.

Preferably said product is suitable for use in a composition for injection, as sublingual tablets, oral tablets, sustained release sublingual tablets, microcapsules, feed premix, pessaries, pre constituted solid dose for nasal spray or drops, aqueous drops, eye wash or drops, or a skin washing solution.

A method as herein described when used to stabilize biological materials.

A method for creating stable sustained release tablets or microcapsules for ingestion by an animal, including a human.

A method for creating a tablet or microcapsules to be administered to an animal, including a human, said tablet having a protective enteric coating. Examples of enteric coating materials which may be used in the invention include cellulose acetate phthalate, cellulose acetate succinate, cellulose acetate trimellitate, hydroxypropylmethyl cellulose phthalate, hydroxypropylmethyl cellulose acetate succinate, polyvinyl acetate phthalate, methacrylic acid/methyl methacrylate copolymer and methacrylic acid/ethylacrylate copolymer.

A method of producing a substantially room temperature stable antidiarrhoea agent as herein described.

A method of producing a substantially room temperature stable growth promotant formulation as herein described.

A method of producing a substantially room temperature stable weight loss agent as herein described.

A method of producing a substantially room temperature stable tablet or microcapsules containing β-1,3-glucan as herein described.

A method of producing a substantially room temperature stable product containing erythropoietin (EPO) as herein described.

A method of producing a substantially room temperature stable product containing interferon as herein described.

A method of producing a substantially room temperature stable product containing *Bifidus*.

A method of producing a substantially room temperature stable product containing *Lactobacilli*.

A method of producing a substantially room temperature stable product containing *Lactobacilli* and *Bifidus*.

A method of producing a substantially room temperature stable product containing alternative probiotics or micro organisms.

Substantially room temperature stable products produced by the method described herein.

A composition comprising a core of microparticles coated with an active and sugar polymer coating layer.

Use of compositions as herein described for the delivery of biological materials to a human or animal.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

PREFERRED EMBODIMENTS

These and other aspects of the present invention, which should be considered in all its novel aspects, will become apparent from the following description, which is given by way of example only. It will be appreciated that, while not explicitly mentioned herein, a number of modifications may be made to the invention without departing from the scope thereof.

BACKGROUND

During tablet manufacturing using fluid bed technology the present inventors discovered that the tablets produced were always free of bacteria even when the raw materials had bacterial counts in excess of 1000 CFU/g (CFU=colony forming units). In order to clarify which of the processing parameters was responsible for the apparent bactericidal effect, the inventors designed an experimental protocol which is described in general terms below.

The experiment was conducted in a Huttlin Turbojet Fluid Bed Coater (BWI Huttlin, Daimlerstrasse 7, D-79585, Steinen, Germany) with a 5 L processing container fitted with three bottom spray three-component spray nozzle jets and standard 20 micron filter bags. Samples of *Lactobacilli* were sourced from Chr. Hansen of 49 Barry Street, Bayswaster, Melbourne, Australia. *Lactobacilli* with *Bifidus* at a ratio of 1:1 was sourced from Gist-Brocade, Australia. These bacteria are anaerobes which easily perish in the presence of oxygen. The trial batch size of the fluidized bed was 4 kg, twice the weight recommended for the 5 L Huttlin Turbojet processing container used, to ensure the fluidized material was close to the processing containers filter giving the best chance for the bacteria to escape through the 20 micron filter. The solid core (tablet granule core materials) comprised 66% w/w dextrose, 13% w/w gelatin, 15% w/w starch. The spraying liquid containing bacteria comprised either $1.16 \times 10^{12}$ CFU *Lactobacilli*, or $3.5 \times 10^{12}$ CFU *Lactobacilli/Bifidus*, with 3% w/w mannitol, 1% w/w egg albumin, 1% w/w glycerol, 1% w/w sodium phosphate buffers and made up to 1000 ml with purified water.

The solid core material was loaded into the Huttlin Turbojet by vacuum and fluidized at a rate of 250 or 300 cubic meter of air/hour. Subsequently, the spray liquid was sprayed into the processing container at a rate of 30 gram/minute. The process was conducted at a product temperature of 40–45° C. The material was dried to less than 5% moisture content at a product temperature of 40° C.

It was discovered that running the experiment with a fluidisation rate set at 250 cubic meters of air/hour was not sufficient. At this rate the fluidized material crashed when 95% of the liquid was sprayed into the solid core. Fluidisation at a rate of 300 cubic meters of air/hour overcame this problem.

Samples of the granules obtained during this process were retained and the rest of the granules were compressed into tablets after blended with a standard tablet lubricant. The granules and the tablets were analysed to assess their live bacterial count. The results obtained are provided in Table 1 below.

TABLE 1

| Sample Description | Theoretical activity in CFU/4 kg time zero | Reported activity in CFU/4 kg time zero | Reported activity in CFU/4 kg sample kept at 4° C. for 60 days |
| --- | --- | --- | --- |
| Chr. Hansen Granules | $1.16 \times 10^{12}$ | $1.70 \times 10^{11}$ | $1.64 \times 10^{11}$ |
| Chr. Hansen Tablet | $1.12 \times 10^{12}$ | $4.40 \times 10^{11}$ | $4 \times 10^{10}$ |
| Gist-Brocade Granules | $3.52 \times 10^{12}$ | $9.80 \times 10^{10}$ | $4.80 \times 10^{10}$ (Lactobacilli only) (No Bifidus detected) |
| Gist-Brocade Tablet | $3.44 \times 10^{12}$ | $6.00 \times 10^{10}$ | $1.2 \times 10^{10}$ (Lactobacilli only) (No Bifidus detected) |

It was extremely surprising to detect the presence of viable bacterial cells in the samples after the treatment the bacterial cells were exposed to in the processing of the granules and tablets; heating, possible total ventilation through the 20 micron filter, mechanical milling, air drying and tablet compression. That a substantially high number of bacteria survived during these experiments did not elucidate why the tablets the inventors had previously produced were bacteria free. The results did, on the other hand, suggest a novel process to prepare samples or products containing live bacteria in a stabilized form.

The suppliers of the *lactobacilli* and *bifidus* cultures indicated that these bacteria are extremely temperature sensitive, and heat labile. When such cultures are processed using freeze-drying, bacterial counts are noted to drop by 90–99%. Further, the suppliers have indicated that the bacteria are also particularly sensitive to standard tablet compression processes and accordingly that a further drop in activity of the bacteria of approximately 99% may be observed.

Accordingly, the inventors have discovered a novel heat drying method which appears to be superior to known industrial methods of preparation, such as freeze-drying. The inventors have further found that bacteria processed in this novel manner (i.e. in micro-capsules) can survive tablet compression pressure around 5 to 8 tons/square inch.

GENERAL DESCRIPTION

The present invention provides a novel way of drying and preserving moisture-sensitive materials, particularly biological materials such as proteins, peptides and plant and animal cells, including micro-organisms. In general terms, the method combines the technologies of fluid bed spray processing and micro-encapsulation.

In general terms, the process involves the spraying of a liquid containing at least an active of interest, in combination with at least one sugar polymer, and a water miscible/soluble solvent, onto an acceptable particulate excipient material (microparticles) which is appropriately fluidized in a processing chamber, at temperatures elevated above room temperature. The coating of said microparticles provides for the stable micro-encapsulation of the active ingredient.

As used herein an "active" generally includes proteins, peptides and cells. However, those of skill in the art to which the invention relates will readily appreciate other materials or active agents which may benefit from preparation according to the invention. It will be appreciated that as used herein the term "proteins", "peptides" and "cells" refer to those which have been produced artificially in the laboratory, via chemical synthesis, or recombinant techniques, in addition to those which are naturally occurring.

The microparticles comprise water soluble gel forming solid particles, preferably having an adhesive surface, consisting of either natural or synthetic polymers or monomers which can tolerate relative high moisture content without turning into liquid or semi solids. For example, the microparticles preferably comprise at least one of acrylate and derivatives, albumin (for example egg albumin (albumen)), alginates, carbomers, carrageenan, cellulose and derivatives, dextran, dextrin, gelatin, polyvinylpyrrolidone (for example Povidone), starch or a combination thereof. Preferably, the microparticles comprise albumin, gelatin, and pregel starch (for example, pregel maize starch). The microparticles are preferably 100 microns in diameter, however, it will be appreciated that alternative sizes may be utilised in the invention; for example 50 micron to 1 mm particle size. It should be noted that the water soluble gel forming solid particles of the microparticles, may be referred to herein as a "hydrogel core".

It will be appreciated that the composition of the microparticles used in the invention ensures the liquid spray material containing the active binds efficiently to the surface of the microparticles without agglomeration or loss.

During processing the microparticles are required to be saturated with moisture to ensure the surface of the particles are not overheated and a thin film is formed on the surface thereof. The composition also has the advantage that it dries in a comparatively slower manner than hard surface particles and also in a continuous manner to give a complete surface coating.

As described briefly above, the spray or coating liquid comprises at least an active, a sugar polymer and a water soluble/miscible solvent. The sugar polymer is preferably mannitol, isomalt, xylitol, polydextrose or dextran.

However, it will be appreciated that alternative polymers may be used depending on the precise nature of the active contained within the solution. Suitable sugar polymers may include, for example, fructose, fruitose, glucose, invert sugar, lactitol, lactose, maltitol, maltose, maltodextrin, sorbitol, sucrose, trehalose, or combinations thereof. The water soluble/miscible solvent is preferably either or both of glycerol or propylene glycol; however, those of general skill in the art to which the invention relates may realize alternative solvents suitable for use in the invention.

The spray or coating liquid may also contain additional constituents such as further proteins, amino acids, diluents, chelating agents, buffers, preservatives, stabilizers, antioxidants, lubricants and other additives which may act to compliment the function of, or stabilize, the particular active contained therein. The precise nature of such additional constituents, will depend on the nature of the active. However, examples each include: amino acids, lysine, glycine, L leucine, isoleucine, arginine, cysteine; proteins, human serum proteins, albumin (for example egg albumin (albumen)), gelatin; buffers, various sodium phosphate buffers, citric/citrate buffers, tris buffer; preservatives, derivatives of hydroxybenzoic acids; antioxidants, vitamin E, ascorbic acid; lubricants, water miscible silicone/silicates; chelating agents, citric acid, EDTA, EGTA. Those of skill in the art will appreciate a variety of other proteins, amino acids, diluents, chelating agents, buffers, preservatives, stabilizers, antioxidants and lubricants which may be suitable for use in the present invention.

The process is preferably conducted in an enclosed sterile environment. As used herein a "sterile environment" is taken to be an environment which is substantially free of contaminating material. Generally such "contaminating material" will comprise microorganisms or the like however, those skilled in the art will appreciate other materials which may be desired not to be present during processing of a product.

The environment in which the process is conducted is preferably free of oxygen to minimise oxidation of actives, for example. This may be achieved by replacing the air contained within the processing chamber, in which the processing of the method of the invention substantially takes place, with an inert gas, preferably nitrogen. However, it will be appreciated that alternative gases may be utilised, such as carbon dioxide.

As briefly mentioned herein before, the microparticles are required to be saturated with moisture. Accordingly, the process is said to be conducted in a moisture saturated environment. In a "moisture saturated environment" the conditions are such that the surface of the microparticles will begin to dissolve changing from a totally solid state to a substantially liquid state. Moisture saturation is achieved in the present invention by over spraying the coating liquid onto the hydrogel core.

The process of the invention may be carried out in any appropriate fluid bed spraying apparatus. In the Examples elucidated herein a CPU Driven Turbojet™ Fluid Bed Coater, manufactured by BWI Huttlin (Daimlerstrasse 7, D-79585, Steinen, Germany) has been used. Those of general skill in the art to which the invention relates will be familiar with such apparatus. However, further information may be readily obtained from the manufacturer if necessary.

It will be appreciated that modifications may be made to the apparatus used in the process of the invention in order to facilitate efficient and effective microencapsulation. For example, the Huttlin Turbojet used in the examples described herein, was custom modified as follows:

The spray nozzle was redesigned such that the centre part of the nozzle (which delivers the liquid spray to the processing chamber) may be removed during operation of the apparatus, for cleaning or unblocking the nozzles. This modification allows for continuous processing.

The central air return column present in the standard Huttlin Turbojet apparatus was rearranged and replaced with a cone-like arrangement such that at high velocity, the fluidized material moves in a vortex-like manner, and at low velocity, circulates in a whirlpool motion. It is considered that such a modification allows for improved coating of the micro particles.

All contact surfaces were extra mirror polished such that they can be readily heat sterilised after the standard Cleaning-In-Place cycle.

Additional compressed air spray nozzles facing the inner surface of the processing container/chamber wall were added surrounding the existing dynamic filter system arrangement. This modification may provide a continuous stream of compressed air flowing from the top of the chamber along the surface of the inner chamber ensuring the working surface in the process container is cleaned continuously. This modification ensures the equipment can be operated continuously without repeat cleaning.

The processing air is so designed that at any stage a recirculating inert gas, such as nitrogen, can be introduced for fluidisation instead of air. This modification may reduce biological protein oxidation and increase anaerobic bacteria stability.

The microencapsulation process of the invention uses an unconventional bottom spray coating operation. That is, spraying of the spray or coating liquid occurs from the bottom of the processing container upwards. As such, it will be appreciated that the spray nozzles are actually embedded within the fluidized bed. Depending on batch size there can be up to thirty eight spraying nozzles operating at the same time.

The spray liquid is processed in such manner that it transforms itself into a continuous glassy film ("bioglass" film) wrapped around the solid surface of the fluid bed particles. The transformation from liquid to glassy solid is rapid, preventing denaturing of the biological protein or microorganism. The active, such as a biological proteins or micro organisms do not suffer in the heat, which is dissipated by the latent heat of evaporation of water.

The process of the present invention preferably involves the over weighting of the microparticles into the processing chamber. In normal fluid bed operation it is recommended by equipment manufacturers not to exceed 50% w/v capacity of the processing chamber. For example, if the processing container is 100 L, processing material weight should not be more than 50 kg. However, the process of the present invention allows for (and it is preferable to do so) the processing weight:container volume to be more than 50% w/v. In this manner, the weight of the microparticles may act like a sieve so that when the encapsulation process is initiated, the spray liquid will not pass through the fluidized microparticles and out through the dynamic filter system resident at the top of the processing chamber.

The method of the invention may be described in general terms as follows:

1 Solid hydrogel particles (microparticles) of a suitable constitution are loaded into the Turbojet by vacuum and fluidized. Fluidization may occur at a rate of between 200 to 500 cubic meters per hour.

2 The microparticles are preferably heated to 30° C. to 80° C., more preferably to 60° C., for approximately one hour with high velocity processing air so they are fluidized in a vortex-like motion, ensuring that the inner part of the microparticles are dry.

3 Microparticle temperature is preferably reduced to 35° C. to 55° C. and the processing air velocity is similarly preferably reduced so that the microparticles move in a whirlpool-type manner.

4 When the micro-particle temperature reaches preferably approximately 40° C. to 50° C., the processing air is preferably replaced with an inert gas, such as nitrogen. This step is preferably held for at least approximately 10 minutes to ensure all the air is replaced with nitrogen.

5 Active is immobilised in an appropriate spray or coating solution. The base solution is preferably heated to 38° C. to allow complete solid dissolution. Prior to Turbojet spray coating the biological materials are added to the base solution (mixing at approximately 60 rpm) and mixed well.

6 A desired quantity of coating solution is then Turbojet Spray Coated onto the fluidized microparticles preferably at high speed (preferably at the highest available speed) so the microparticles are saturated with moisture but still able to freely flow in a whirlpool manner. Spray coating preferably takes place at a rate of 30 grams to 60 grams per minute. The spraying of said coating solution or liquid onto the microparticles occurs from beneath the fluidized bed.

7 Turbojet coating speed is slowed to preferably between 10 grams to 20 grams per minute when the microparticles are saturated with moisture, to ensure the bed of microparticles is continuously flowing in a whirlpool manner. In this manner the coating solution containing the biological protein is continuously dehydrated in a moisture free nitrogen environment, for example. The product is typically dried to result in a water activity of less than 0.25.

It will be appreciated that the above processing steps and parameters may be altered to accommodate the production of various product forms, or products comprising different actives. Alterations may be made for example to: the inlet process air temperature, the product temperature, fluidized air volume, liquid spraying speed, spray liquid temperature, spray liquid viscosity, spray liquid solid content, total core surface area, water solubility of core, humidity of inlet air, compressed air spraying pressure, the apparatus filter pore size, and the frequency of auto dedusting. Where an alteration is made to one parameter, a person of general skill in the art to which the invention relates will readily be able to identify any corresponding adjustments which may be required in another parameter to compensate for the first said alteration. In addition, by increasing the molecular weight of the hydrogel core sustained release solid dosage can be created.

Further, additional coating steps may be added to the above general process according to the invention, in order to obtain products having desired characteristics. For example, prior to or after the drying step, the resultant product, or microcapsules, may be coated with further coatings. Those of skill in the art to which the invention relates will immediately realize situations where this may be advantageous; for example, where a resultant product is desired to be administered orally, enteric coatings which may protect the product from degradation in the stomach, and/or, those which allow for sustained or slow release of the active therefrom may be utilized. Generally such further coating will be carried out at a similar coating rate as that used for coating the microparticles with the initial coating liquid.

The batch size for processing may vary according to the volume of the processing chamber of the apparatus used, and whether overloading thereof is required. In the Examples which are described herein, the batch size is typically 4 kg. "Batch size" refers to the total solids used in the processing of the product and constitutes solids contained in both the microparticles, coating solution, and any additional coating solutions used to formulate the product. Accordingly, as used herein percentages of particular constituents are expressed in terms of the percentage of the total batch size.

Various other modifications will become apparent from the Examples provided herein.

The invention is now further elucidated by reference to the following specific non limiting examples, and figures.

In the figures:

FIG. 1: Sublingual delivery of EPO in rats. Reticulocyte counts show it as $10^{10}$/L measured from withdrawn blood samples are plotted against days on or after treatment. The normal range is depicted by (two thick lines); treatment groups were by subcutaneous injections (line with diamond in the middle) of 50 IU on day one; sublingual deliver of 125 IU EPO (line with square in the middle) on days one, two and three; sublingual delivery of 125 IU EPO (a line with light coloured triangle delivered on days one, two, three, four and five.

Figure 2:
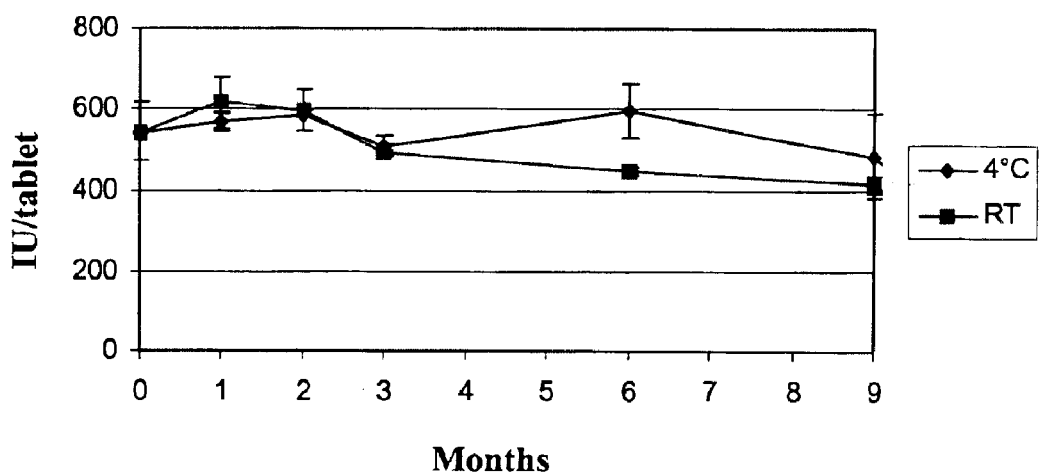

FIG. 2: Shows stability of EPO tablets over nine months at 4° C. (a line with a diamond through it) and a room temperature (a line with a square through it).

EXAMPLES

Example 1

Stabilization of Microorganisms

Example 1A

Eight liters of live *Bifidus* culture was obtained from an original 3000 L liquid culture from Sine Pharmaceutical Co., Ltd. #905, Xinjinqiao Rd., Pudong, Shanghai, P.R. China. Data supplied from the manufacturer established that 3000 L of fermentation liquid contains a total of $3 \times 10^{16}$ CFU (colony forming units) and yields approximately 8.3 kg of freeze dry material containing a total of $2.16 \times 10^{14}$ CFU of *Bifidus*; that is, after freeze drying, there is reduction of approximately 99% live bacteria population.

After arrival in the laboratory a sample of the culture was tested for stability at 4° C. At time zero $2.43 \times 10^{16}$ CFU/3000 L was recorded. After storage for fourteen days under 4° C., the count was reduced to $1.5 \times 10^{14}$ CFU/3000 L; that is, about one in 1500 cells survived after two weeks storage at 4° C.

The liquid culture, containing various sugar additives (as described below) was processed according to the invention in the following manner:

1. Solid micro-particle core (hydrogel core) material was loaded into the Huttlin Turbojet by vacuum.
2. The microparticles were fluidized and heated to 60° C. for one hour.
3. The micro-particle core temperature was reduced to 40° to 45° C.
4. The process air was replaced with nitrogen and flushed for ten minutes.
5. Microparticles fluidized at a rate of 300 cubic meters of air/hour.
6. *Bifidus* coating liquid was turbojet coated onto the hydrogel core particles under saturated moisture conditions at a rate of 30 gram/minute.
7. Resultant product dried to less than 0.25 water activity.
8. Samples of coated microcapsules were tested as time zero and after storage at 4° C., 25° C. and 40° C.

This bioencapsulation process was conducted using four different combinations of micro-particle, or hydrogel core, and coating liquid formulations as indicated below.

| SINE RX1 | 4 kg Batch |
|---|---|
| Hydrogel Core 1 | |
| Dextrose | 2.64 kg |
| Gelatin | 0.52 kg |
| Starch | 0.60 kg |
| Coating Liquid 1 | |
| $1 \times 10^{10}$ CFU Bifidus | |
| Mannitol | 0.20 kg |
| Sodium phosphate buffer | 0.04 kg |
| Purified water to | 1.00 kg |
| SINE RX2 | 4 kg Batch |
| Hydrogel Core 2 | |
| Dextrose | 2.44 kg |
| Gelatin | 0.52 kg |
| Starch | 0.60 kg |
| Egg Albumin | 0.20 kg |
| Coating Liquid 2 | |
| $1 \times 10^{10}$ CFU Bifidus | |
| Mannitol | 0.20 kg |
| Sodium phosphate buffer | 0.04 kg |
| Purified water to | 1.00 kg |
| SINE RX3 | 4 kg Batch |
| Hydrogel core 3 | |
| Dextrose | 2.44 kg |
| Gelatin | 0.52 kg |
| Starch | 0.60 kg |
| Egg Albumin | 0.20 kg |
| Coating Liquid 3 | |
| $1 \times 10^{10}$ CFU Bifidus | |
| Dextran | 0.20 kg |
| Sodium phosphate buffer | 0.04 kg |
| Purified Water to | 1.00 kg |
| SINE RX4 | 4 kg Batch |
| Hydrogel core 4 | |
| Dextrose | 2.44 kg |
| Gelatin | 0.52 kg |
| Starch | 0.60 kg |
| Egg Albumin | 0.20 kg |

-continued

| Coating Liquid 4 | |
|---|---|
| $1 \times 10^{10}$ CFU Bifidus | |
| Egg Albumin | 0.20 kg |
| Sodium phosphate buffer | 0.04 kg |
| Purified Water to | 1.00 kg |

Results recorded are listed in Table 2 below and expressed as CFU equivalent to 3000-L original concentration.

TABLE 2

| Formulation Code | Time zero PRE Bioencapsulation | Time zero POST Bio-encapsulation | Four weeks POST Bio-encapsulation |
|---|---|---|---|
| SINE RX1 at 4° C. | $1.5 \times 10^{14}$ | $6.00 \times 10^{12}$ | $6.00 \times 10^{13}$ |
| SINE RX2 at 4° C. | $1.5 \times 10^{14}$ | $2.70 \times 10^{12}$ | $3.69 \times 10^{13}$ |
| SINE RX3 at 4° C. | $1.5 \times 10^{14}$ | $2.70 \times 10^{12}$ | $9.90 \times 10^{12}$ |
| SINE RX4 at 4° C. | $1.5 \times 10^{14}$ | $1.41 \times 10^{13}$ | $1.29 \times 10^{12}$ |
| Average | | | $2.99 \times 10^{13}$ |
| SINE RX1 at 25° C. | $1.5 \times 10^{14}$ | $6.00 \times 10^{12}$ | $1.38 \times 10^{13}$ |
| SINE RX2 at 25° C. | $1.5 \times 10^{14}$ | $2.70 \times 10^{12}$ | $2.04 \times 10^{13}$ |
| SINE RX3 at 25° C. | $1.5 \times 10^{14}$ | $2.70 \times 10^{12}$ | $6.30 \times 10^{11}$ |
| SINE RX4 at 25° C. | $1.5 \times 10^{14}$ | $1.41 \times 10^{13}$ | $6.00 \times 10^{12}$ |
| Average | | | $1.02 \times 10^{13}$ |
| SINE RX1 at 40° C. | $1.5 \times 10^{14}$ | $6.00 \times 10^{12}$ | <10000 |
| SINE RX2 at 40° C. | $1.5 \times 10^{14}$ | $2.70 \times 10^{12}$ | $4.5 \times 10^{11}$ |
| SINE RX3 at 40° C. | $1.5 \times 10^{14}$ | $2.70 \times 10^{12}$ | <10000 |
| SINE RX4 at 40° C. | $1.5 \times 10^{14}$ | $1.41 \times 10^{13}$ | <10000 |

The results indicate ten times more live *Bifidus* survive the processing according to the present invention compared to conventional freeze-drying processes. The reaction referred to as SINE RX2 gave the best stability results.

It was found that during processing of Sine RX1 moisture was not effectively picked up by the dextrose contained within the hydrogel core. When albumin was added to the hydrogel core formulation (see RX2 to RX4) processing was satisfactory.

Example 1B

Further batches of *Bifidobacterium bifidum* 6-1 were imported from Sine Pharmaceutical Co., Ltd. #905, Xinjinqiao Rd., Pudong, Shanghai, P.R. China. The culture used in Example 1A was thought to contain some waste material which may contribute to instability of the bacteria in the final bioencapsulated solid micro capsules. Accordingly, the culture used in the present example had all waste material removed, was concentrated and resuspended in buffer solutions. The culture was assayed on arrival from the manufacturer and a sample was also assayed just prior to use. Results indicated a bacterial count of $4.1 \times 10^8$ CFU/L.

| SINE RX6 | 4 kg Batch |
|---|---|
| Hydrogel core 6 | |
| Pregel Maize Starch | 3.10 kg |
| Egg Albumin | 0.40 kg |
| Coating Liquid 6 | |
| Bifidus $8.2 \times 10^8$ CFU | |
| Mannitol | 0.10 kg |
| Glycerol | 0.30 kg |
| Sodium Alginate | 0.06 kg |
| Sodium phosphate buffer | 0.04 kg |
| Purified water to | 1.00 kg. |

| SINE RX7 | 4 kg Batch |
|---|---|
| Hydrogel core 7 | |
| Pregel Maize Starch | 2.44 kg |
| Gelatin | 0.52 kg |
| Starch | 0.60 kg |
| Egg Albumin | 0.20 kg |
| Coating Liquid 7 | |
| Bifidus $4.2 \times 10^8$ CFU | |
| Mannitol | 0.05 kg |
| Glycerol | 0.15 kg |
| Sodium Alginate | 0.06 kg |
| Sodium phosphate buffer | 0.04 kg |
| Purified water to | 1.00 kg |

| SINE RX8 | 4 kg Batch |
|---|---|
| Hydrogel core 8 | |
| Pregel Maize Starch | 2.54 kg |
| Gelatin | 0.52 kg |
| Starch | 0.60 kg |
| Egg Albumin | 0.20 kg |
| Coating Liquid 8 | |
| Bifidus $4.2 \times 10^8$ CFU | |
| Mannitol | 0.025 kg |
| Glycerol | 0.075 kg |
| Sodium phosphate buffer | 0.040 kg |
| Purified water to | 1.00 kg. |

| SINE RX9 | 4 kg Batch |
|---|---|
| Hydrogel core 9 | |
| Pregel Maize Starch | 2.52 kg |
| Gelatin | 0.52 kg |
| Starch | 0.60 kg |
| Egg Albumin | 0.20 kg |
| Coating Liquid 9 | |
| Bifidus $4.2 \times 10^8$ CFU | |
| Mannitol | 0.025 kg |
| Glycerol | 0.075 kg |
| Sodium Alginate | 0.020 kg |
| Sodium phosphate buffer | 0.040 kg |
| Purified water to | 1.00 kg. |

Processing was carried out according to the protocol used in Example 1A.

Results recorded are listed in Table 3 below and expressed as CFU in 4 kg of microcapsules.

TABLE 3

| Formulation Code | Time zero PRE Bio-encapsulation | Time zero POST Bio-encapsulation | Two months POST Bioencapsulation |
|---|---|---|---|
| SINE RX6 at 4° C. | $8.4 \times 10^8$ | $1.56 \times 10^8$ | $2.24 \times 10^8$ |
| SINE RX7 at 4° C. | $4.2 \times 10^8$ | $5.32 \times 10^7$ | $6.00 \times 10^7$ |
| SINE RX8 at 4° C. | $4.2 \times 10^8$ | $4.72 \times 10^7$ | $4.04 \times 10^7$ |
| SINE RX9 at 4° C. | $4.2 \times 10^8$ | $4.48 \times 10^7$ | $2.36 \times 10^7$ |
| SINE RX6 at 25° C. | $8.4 \times 10^8$ | $1.56 \times 10^8$ | $1.64 \times 10^8$ |
| SINE RX7 at 25° C. | $4.2 \times 10^8$ | $5.32 \times 10^7$ | $1.56 \times 10^7$ |
| SINE RX8 at 25° C. | $4.2 \times 10^8$ | $4.72 \times 10^7$ | $2.76 \times 10^7$ |
| SINE RX9 at 25° C. | $4.2 \times 10^8$ | $4.48 \times 10^7$ | $1.40 \times 10^7$ |
| SINE RX6 at 40° C. | $8.4 \times 10^8$ | $1.56 \times 10^8$ | <100 |
| SINE RX7 at 40° C. | $4.2 \times 10^8$ | $5.32 \times 10^7$ | <100 |

TABLE 3-continued

| Formulation Code | Time zero PRE Bio-encap-sulation | Time zero POST Bio-encap-sulation | Two months POST Bioencapsulation |
|---|---|---|---|
| SINE RX8 at 40° C. | $4.2 \times 10^8$ | $4.72 \times 10^7$ | <100 |
| SINE RX9 at 40° C. | $4.2 \times 10^8$ | $4.48 \times 10^7$ | <100 |

It is apparent from the results that the addition of glycerol to the hydrogel core particles further enhances the biological stability of *Bifidus*. It was observed that the addition of alginate to the coating liquid improved fluidisation but did not significantly affect the stability of the bacterium in the final product.

The results obtained from this example again demonstrate that the process of the invention may be considered superior to that of currently used processing techniques, for example freeze-drying; in SINE RX6 it is seen that 1 in 5 bacteria survived processing according to the invention as compared to a reported 1 in 100 in the traditional freeze-drying method.

Example 2

Stabilization of Enzymes

Enzymes are biological proteins which have applications in a variety of industries; for example, they are used in food processing, as animal feed additives, and as human and animal medications.

Example 2a

Stabilized Enzymes Incorporated into Feed as Growth Promotant (Enzyme Growth Promotant 2)

Enzymes such as proteases, lipases, amylases, and cellulases, for example, are common additives to animal feed. These enzymes help to increase the bioavailability of the feed.

Animal feed is often manufactured such that the enzymes, together with vitamins and minerals such as copper sulfate and iron, are mixed into the feed. The feed is then generally palletised by steam injection and extrusion. The operating temperature of the feed during palletisation can reach 80° C. and above for approximately ten minutes. Under such conditions many of the enzymes added to the mix may be denatured. In addition, when such feed enters the stomach of an animal, many of the enzymes may be denatured due to the acidic environment therein.

To counter the loss of enzymatic activity due to feed palletisation and the acidic environment in the stomach, current practice is to add massive quantities of enzymes into the feed premix in the hope that at least some of the enzymes will survive.

Accordingly while the use of enzymes in animal feed is theoretically beneficial, the efficacy has not been consistently demonstrated to be economically viable.

Where the added enzymes are sufficiently protected from the harmful environmental factors to which they may be exposed, there may be significant economic and growth benefits. Australian Patent Application AU07872187 describes a growth promotant comprising microgranules having a core, consisting of one or more immobilised enzymes, encapsulated within a water soluble film and coated with a protective enteric coating. Such a product may help overcome the problems associated with degradation of feed enzymes.

AU07872187 describes a method of producing such a product described in the previous paragraph which typically involves freeze-drying and milling. The present example demonstrates that the method of the present invention may be used to produce an equivalent product, which may significantly reduce the cost of production.

The formulation for the enzyme growth promotant 2 is as follows, expressed in terms of a 4 kg batch size (% w/w):

Hydrogel core: Pregel Maize Starch 67.5%, polyvinylpyrrolidone (Povidone) 10%.

Coating liquid: Protease $2 \times 10^5$ Vitapharm Protease Units, Amylase $4.3 \times 10^6$ Vitapharm Amylase Units, Lipase 50 Vitapharm Lipase Units, Cellulase $2 \times 10^4$ Vitapharm Cellulase Units, mannitol 2.5%, glycerol 7.5%, polyvinylpyrrolidone (Povidone) 1.5%, sodium phosphate buffer to pH 7 1%, purified water to 1 kg.

Enteric Coating

Solution (1 L batch): Cellulose acetate phthalate 10%, sodium hydroxide qs to pH 6, water purified to 100%.

Final Acid

Rinse Solution: Citric acid qs to pH 3, purified water to 1 L.

The growth promotant of the present example is preferably used at a rate of 1 kg/ton feed.

The growth promotant formulation was processed according to the invention using the following protocol:

1 Hydrogel core material is vacuum loaded into the Huttlin Turbojet chamber, fluidized and heated to 60° C. for one hour.
2 Hydrogel core product temperature reduced to 45° C.
3 The content of the chamber is fluidized at a rate of 300 cubic meters per hour.
4 Coating liquid turbojet coated onto the hydrogel core under saturated moisture conditions at a rate of 30 g/minute.
5 Product dried to less than 5% moisture content.
6 Enteric coating solution turbojet coated onto the core at a rate of 30 g per minute.
7 Citric acid solution turbojet coated onto the core at a rate of 30 g per minute. The acid acts to reconvert the sodium cellulose acetate phthalate back to cellulose acetate phthalate offering the enzymes enteric protection through the stomach.

It is observed that the process of the invention requires one tenth of the processing time compared with the previous method of processing described in AU07872187, and also reduces production costs by up to 50%.

In addition, it is noted and was observed that the process does not use any organic solvents or aldehydes, the entire production can be performed in an enclosed environment in one step, exposure of operators to enzymes is greatly reduced and only half the cellulose acetate phthalate is required to offer the same enteric protection.

Furthermore, the process resulted in a product which is stable at room temperature for at least two years.

The formulation and process of the present example may be modified by providing an additional final 5% w/w wax coating, such as low melting point macrogol or PEG, for example. In this case, it is believed the microcapsules may be incorporated into a feed mix prior to pelletization, with minimal, if any, disruption to enzyme structure; the additional wax coating is able to withstand a short burst of steam and accordingly take up the majority of the heat used during pelletization.

Example 2b

Stabilized Enzymes as Weight Loss Supplement

During studies conducted to determine the appropriate dose rate of the growth promotant 2 described above, it was observed that dosing at 1 kg/ton feed gives the optimum feed conversion. However, where the dose rate is increased and reaches 10 kg/ton feed, the growth promotant formulation is noted to induce significant weight loss.

Accordingly, a weight loss enzyme supplement was formulated and two open trials were conducted in humans.

| The weight loss supplement comprised: | 4 kg Batch |
|---|---|
| Hydrogel core | |
| Pregel Maize Starch | 2.70 kg |
| Polyvinylpyrrolidone (Povidone) | 0.40 kg |
| Coating Liquid | |
| Protease 2 × $10^6$ Vitapharm Protease Units | |
| Amylase 4.3 × $10^7$ Vitapharm Amylase Units | |
| Lipase 500 Vitapharm Lipase Units | |
| Cellulase 2 × $10^5$ Vitapharm Cellulase Units | |
| Mannitol | 0.10 kg |
| Glycerol | 0.30 kg |
| Polyvinylpyrrolidone (Povidone) | 0.06 kg |
| Sodium phosphate | |
| buffers to pH 7 | 0.04 kg |
| Purified water to | 1.00 kg |
| Enteric Coating Solution | |
| Cellulose Acetate Phthalate | 0.40 kg |
| Sodium Hydroxide qs to pH 6 | |
| Water purified to | 4 kg |
| Final Acid Rinse Solution | |
| Citric Acid qs to pH 3 | |
| Purified water to | 1.00 kg |

The weight loss supplement was processed according to the invention using the protocol used for the preparation of the enzyme growth promotant 2, described above.

Following processing, the microcapsules were packed in moisture proof sachets, in lots of 1 g. A dosage of one sachet mixed in water was taken before each meal.

Example 2b(i)

Weight Loss Study 1

Nine volunteers were recruited to determine whether the composition has any weight loss effect, when taken as indicated above. Result are given in Table 4 below:

TABLE 4

| Subject | Body weight in kg Week 0 | Body Weight in kg End of Six weeks |
|---|---|---|
| 1 | 125 | 116.4 |
| 2 | 107 | 101.5 |
| 3 | 105 | 97 |
| 4 | 100 | 97 |
| 5 | 79 | 69 |
| 6 | 78 | 72 |
| 7 | 73.5 | 66.3 |
| 8 | 73 | 69 |
| 9 | 68.3 | 61.5 |
| Total | 808.8 | 746.7 |
| Mean | 90 | 83 |

A mean weight loss per person of approximately 1.08 kg per week, or 7 kg over six weeks, was observed.

Weight Loss Study 2

A second study of twenty volunteers was conducted under the supervision of a medical practitioner. Dosage rates were as for "Weight loss study 1".

The results of this study are collected in Table 5 below.

TABLE 5

| Subject | Body weight in kg Week 0 | Body Weight in kg End of three weeks |
|---|---|---|
| 1 | 128 | 120 |
| 2 | 126 | 121 |
| 3 | 115 | 109 |
| 4 | 108 | 100 |
| 5 | 102 | 101 |
| 6 | 102 | 97 |
| 7 | 97 | 92 |
| 8 | 94 | 93 |
| 9 | 92 | 90 |
| 10 | 92 | 88 |
| 11 | 89 | 85 |
| 12 | 85 | 84 |
| 13 | 83 | 81 |
| 14 | 82 | 78 |
| 15 | 78 | 76.5 |
| 16 | 77 | 70 |
| 17 | 77 | 70 |
| 18 | 74 | 71 |
| 19 | 73 | 72 |
| 20 | 68 | 60 |
| Total | 1842 | 1758.5 |
| Mean | 92.1 | 88 |

Mean weight loss per person was approximately 1.37 kg per week, or 4.1 kg over three weeks.

The results obtained from the two isolated studies described indicated that the enzyme formulation described herein may be an effective weight loss supplement.

Example 2c

Stabilized Bromelain as Anti-Diarrhoea Medication

It has previously been demonstrated that proteases can be used for treatment of intestinal pathogens in animals, including humans; AU07858587 and AU02367392. Compositions for delivery of such proteases have been described comprising: (i) granules comprising a biologically active material in association with a weak base and partially coated with a delayed release material soluble in intestinal juice; (ii) an acidifying agent having a pH between 1.6 to 6; and (iii) a gel forming agent. The resulted preparations are able to modify the host intestinal surface so that it is not susceptible to bacterial colonisation. Accordingly, the preparation is useful for prevention and treatment of diarrhoea.

The example elucidated below provides an improved method of manufacturing such an antidiarrhoea formulation.

| The antidiarrhoea formulation comprised: | 4 kg Batch |
|---|---|
| Hydrogel core | |
| Pregel Maize Starch | 2.914 kg |
| Polyvinylpyrrolidone (Povidone) | 0.40 kg |
| Coating Liquid | |
| Bromelain | 0.053 kg |
| Cysteine | 0.053 kg |
| Mannitol | 0.10 kg |
| Glycerol | 0.30 kg |
| Polyvinylpyrrolidone (Povidone) | 0.06 kg |

-continued

| The antidiarrhoea formulation comprised: | 4 kg Batch |
|---|---|
| Sodium phosphate buffers to pH 7 | 0.04 kg |
| Purified water to | 1.00 kg |
| Enteric Coating Solution | |
| Cellulose Acetate Phthalate | 0.08 kg |
| Sodium Hydroxide qs to pH 6 | |
| Purified water to 8 kg of total batch size | |
| Final Acid Rinse Solution | |
| Citric Acid qs to pH 3 | |
| Purified water to | 1.00 kg |

The antidiarrhoea formulation was processed according to the invention using the following protocol:
1 Hydrogel core loaded into the Huttlin Turbojet processing chamber by vacuum, fluidized and heated up to 60° C. for one hour.
2 Hydrogel core product temperature reduced to 45° C.
3 Hydrogel bed fluidized at a rate of 300 cubic meters per hour.
4 Hydrogel core turbojet coated with coating liquid under saturated moisture conditions at 30 g/minute.
5 Product dried to less than 5% moisture content.
6 Enteric coating solution turbojet coated onto core at a rate of 30 g/minute.
7 Citric acid solution turbojet coated onto the core at a rate of 30 g/minute; the acid reconverting the sodium cellulose acetate phthalate to cellulose acetate phthalate providing enteric protection for the enzymes within the formulation.

It was observed that this process requires only one twelfth to the processing time compared with conventional methods used to produce such a product. Further, one twentieth of the amount bromelain is required in the formulation (due to increased stability of bromelain within the bioglass matrix).

In addition, it is noted that the entire production can be performed in an enclosed environment in one step, exposure of operators to enzymes is greatly reduced and only one fifth the cellulose acetate phthalate is required to offer the same enteric protection as that gained from the known product described above.

Overall, the production cost is estimated to be reduced to one fifth of that where conventional methods are used to create an equivalent antidiarrhoea formulation.

Furthermore, it was observed that the process resulted in a product which is stable at room temperature for at least two years.

Example 2c(i)

Animal Studies Involving Antidiarrhoea Formulation

A study of the efficacy of the formulation produced according to Example 2c as an antidiarrhoea treatment was conducted at the Animal Husbandry Research Institute, Jinin Province, China. Ninety new born piglets of approximately same weight and age were used in the study.

The piglets were randomly divided into two groups, equal in sex, weight and age. One group was designated for treatment with a Bromelain Preparation according to Example 2c and the other half were used as a control group. 0.75 g of the Bromelain Preparation (Example 2c) was mixed with 8.5 g of water into a paste on the day of use. A first dose of 10 ml was given to the treatment group at day seven after birth and repeated at day ten. The control group received no treatment. Observation of diarrhoea incidence was recorded up to day forty five.

Results are collected in Table 6:

TABLE 6

| | Treatment Group | Control |
|---|---|---|
| Number of animals | 45 | 45 |
| Birth weight (kg) average | 1.40 | 1.35 |
| Vaccination against diarrhoea | Yes | Yes |
| Weaning weight (kg) average | 11.80 | 11.30 |
| Total weight gained | 10.40 | 9.95 |
| Daily weight gained | 249 g | 237 g |
| Feed consumed | 13 kg | 12.7 kg |
| Feed conversion | 1.25 | 1.29 |
| Pigs that has diarrhoea | 3 | 8 |
| Diarrhoea incidence (%) | 6.7 | 17.8 |
| Animal alive (%) | 100 | 100 |
| Diarrhoea days | 3 | 5 |
| Other medication used | 6 | 10 |

All piglets used in this trial were vaccinated against diarrhoea. Nonetheless, the treatment group, after two doses of the bromelain preparation, showed significant weaning weight gain (0.5 kg), reduced diarrhoea incidence (6.7 versus 17.8), reduced severity (three days versus five days) and reduced number of other medications used (6 versus 10) compared to control group.

Example 2d

Stabilized Enzyme Bromelain Plus β Glucan (B&B Preparation) as Anti-Diarrhoea Medication Addition of β-1,3-glucan to the Bromelain Preparation of Example 2c potentates the antidiarrhoea action of bromelain.

B-1,3-glucan, is considered an effective natural non-specific immunostimulant with free-radical scavenging properties. It is thought to act by activating macrophages, which play an essential and pivotal role in the initiation and maintenance of the immune response in animals, including humans.

B-1,3-glucan is known to be orally effective, completely safe and non-toxic. There are several different types of β glucan with different levels of activity, the majority of which are inert and used as simple food fillers. B-1,3-glucan, is however the most active β glucan, and may be obtained from the cell wall of yeast.

B-1,3-glucan may be considered useful in the treatment of many immune-related indications, such as stress-related immunosuppression, for example, has been shown to act synergistically with antibiotics and antiviral medications and to exhibit antifungal properties. Accordingly, β-1,3-glucan may be considered a suitable adjuvant for an improved life-style. Those of general skill in the art to which this invention relates will readily be able to identify animal indications which may benefit from the administration of β-1,3-glucan.

The B&B Preparation of the present example comprises, in the context of an 8 kg batch size:

|  | 4 kg Batch |
|---|---|
| Hydrogel core for Bromelain | |
| Pregel Maize Starch | 2.861 kg |
| Polyvinylpyrrolidone (Povidone) | 0.40 kg |
| Coating Liquid | |
| Bromelain | 0.106 kg |
| Cysteine | 0.106 kg |
| Mannitol | 0.100 kg |
| Glycerol | 0.300 kg |
| Polyvinylpyrrolidone (Povidone) | 0.060 kg |
| Standard sodium phosphate buffer to pH 7 | 0.040 kg |
| Purified water to | 1.00 kg. |
| Hydrogel core for B-1,3-glucan | |
| Gelatin | 2.861 kg |
| Egg Albumin | 0.400 kg |
| Coating Liquid | |
| B-1,3-glucan | 0.106 kg |
| Mannitol | 0.100 kg |
| Glycerol | 0.300 kg |
| Polyvinylpyrrolidone (Povidone) | 0.060 kg |
| Standard sodium phosphate buffer to pH 7 | 0.040 kg |
| Purified water to | 1.00 kg |
| Enteric Coating Solution | |
| Cellulose Acetate Phthalate | 0.16 kg |
| Sodium Hydroxide qs to pH 6 | |
| Purified water to 8 kg of total batch size | |
| Final Acid Rinse Solution | |
| Citric Acid qs to pH 3 | |
| Purified water to | 2.00 kg |

The bromelain microcapsules were processed according to the invention using the following protocol:
1 Hydrogel core for bromelain loaded into the Huttlin Turbojet chamber by vacuum, fluidized and heated up to 60° C. for one hour.
2 Hydrogel core product temperature reduced to 45° C.
3 Hydrogel bed fluidized at a rate of 300 cubic meters per hour.
4 Coating liquid turbojet coated onto the hydrogel core under saturated moisture conditions at a rate of 30 g/minute.
5 Product dried to less than 5% moisture content.
6 Sodium cellulose acetate phthalate solution turbojet coated onto the core product at a rate of 30 g/minute.
7 Citric acid solution turbojet coated onto the core as a final coat at 30 g/minute; the acid acts to convert the sodium cellulose acetate phthalate to cellulose acetate phthalate providing enteric protection for the enzymes within the formulation.

The β-1,3-glucan microcapsules were processed according to the invention using the following protocol:
1 Hydrogel core material for β-1,3 glucan loaded into the Huttlin Turbojet chamber by vacuum, fluidized and heated up to 60° C. for one hour.
2 Hydrogel core product temperature reduced to 45° C.
3 Process air replaced with nitrogen and flushed for ten minutes.
4 Hydrogel bed fluidized at a rate of 300 cubic meters per hour.
β-1,3 glucan coating turbojet coated onto the hydrogel core under saturated moisture conditions at a rate of 30 g/minute.
6 Resultant product dried to less than 5% moisture content.
7 Sodium cellulose acetate phthalate solution turbojet coated onto the core product at a rate of 30 g/minute.
8 Citric acid solution turbojet coated onto the core as a final coat at a rate of 30 g/minute; the acid acts to convert the sodium cellulose acetate phthalate to cellulose acetate phthalate providing enteric protection for the enzymes within the formulation.

The B&B formulation is then prepared by mixing 4 kg of the bromelain microcapsules with 4 kg of the β-1,3 glucan microcapsules.

Using this protocol, each 750 mg of B&B Preparation contains 10 mg bromelain and 10 mg β-1,3-glucan.

In conducting the procedure described in this Example it was noted that the β-1,3-glucan raw material is a very fine powder with a particle size of less than 5 micron in dry form. In liquid form, it forms a fine suspension with a particle size less than 2 microns. Accordingly, to fully capture the active ingredients, a more soluble hydrogel based gelatin has to be used.

It was further noted that in most cases a better hydrogel is obtained using gelatin. However, gelatin is comparatively expensive and pregel starch, for example pregel maize starch, may provide a more economical base for said hydrogel.

A unit dose is prepared by mixing 750 mg of B&B Preparation with 8.5 g of water to make a 10 ml paste.

The recommended dosage for prevention of diarrhoea in piglets is 10 ml at day one of birth, repeat dosing in day five. In farms with a serious history of diarrhoea, dosing may be repeated at day ten and day thirteen.

Example 2d(i)

Field Trials Involving the Use of B&B Preparation

A field trial was conducted in Shangdong, China, to test the efficacy of Bromelain Plus B glucan Preparation in prevention and treatment of diarrhoea in piglets.

B&B Preparation was prepared as in Example 2d. Other medications used in the trial were those standard in the field of animal farming and management.

The trial was conducted at the Breeding Good Pig Farm of Dezhou Husbandry Bureau, which produces over 10,000 pigs annually and which has an incidence of diarrhoea of approximately 40% to 50%.

Nine litters randomly selected were divided into three groups (three litters/group). Two groups were designated as treatment groups, and the third group as a control. A total of ninety seven piglets (Large White York piglets of mixed sex) were included in the trial.

Litters were monitored for a period of twenty six days from the time of first administration of B&B Preparation.

All piglets in treatment groups and control group were vaccinated and given the same medication when sick (presenting diarrhoea and/or associated symptoms).

The trial design is summarised in Table 7 below.

TABLE 7

| Groups | No of pigs | Given dose (5 ml) | Appendix |
|---|---|---|---|
| Treatment 1 | 34 | Day 1 one dose, repeat in day 5 | Monitor the efficacy of yellow scours |

TABLE 7-continued

| Groups | No of pigs | Given dose (5 ml) | Appendix |
|---|---|---|---|
| Treatment 2 | 31 | Day 1 one dose, repeat in day 5, 10 and 13. | Monitor the efficacy of yellow and white scours |
| Control | 32 | No Bromelain Preparation given | Normal medications |

Results of the trial are summarised in Table 8 below.

TABLE 8

| Groups | Number of piglets | Incidence of scour (%) | MDWG (g) (mean daily weight gain) | Mortality | Comments |
|---|---|---|---|---|---|
| Treatment 1 | 34 | 5.1 | 164 | 1 | Scour |
| Treatment 2 | 31 | 4.2 | 178 | 1 | Starvation |
| Control | 32 | 17.59 | 169 | 1 | Scour |

As is seen from Table 8, the results of the trial demonstrate that the incidence of scours in trial groups are 5.10%, 4.2% and 17.59% for treatment group 1, treatment group 2 and the control group respectively. In other words, there was an observed reduction in the incidence of diarrhoea of approximately 70% between the treatment groups and the control groups. This demonstrated B&B Preparation has a remarkable efficacy in the prevention and/or treatment of diarrhoea in piglets.

No significant difference was observed in mean daily weight gains (MDWG) between groups (164 g per day, 178 g per day, and 169 g per day).

Furthermore, the results suggest that administering the preparation twice provides more efficient improvement of the animal's health.

Overall, this trial indicates that B&B preparation according to the invention has efficacy for preweaning scour, and against non specific E.coli diarrhoea. The inventors believe the formulation will have application to other animals, including humans. Those of ordinary skill in the art to which the invention relates will readily be able to modify or adapt the formulation such that it is suitable for administration to animals other than pigs.

Example 3

Slow Release Sublingual Stabilized Biological

Example 3a

Slow Release Sublingual Stabilized β-1,3-glucan Tablets

As previously discussed, β glucans are effective orally. However, when administered orally a substantial dosage is generally required to achieve the desired immunomodulatory effect. A dosage range of anywhere between 10 mg to 2000 mg per day has been recommended, depending on the source of β glucan. The great range in recommended dosages it thought to be due to variation in purity, and bioavailability, of the β glucan products on the market.

The present example provides a formulation of slow release sublingual β-1,3-glucan which when properly stabilized (via the process of the present invention, for example) and delivered to a specific mucosal surface, may be clinically active at a dose of 10 mg per day.

A product according to the present example may be suitable for the treatment or alleviation of symptoms of an allergic condition, for example, hayfever.

An example formula for a slow release sublingual β-1,3-glucan tablet, processed according to the invention, may comprise the following constituents:

| | 4 kg Batch |
|---|---|
| Hydrogel core | |
| Gelatin | 2.527 kg |
| Polyvinylpyrrolidone (Povidone) | 0.400 kg |
| Egg Albumin | 0.400 kg |
| Coating Liquid | |
| β-1,3-glucan | 0.200 kg |
| Mannitol | 0.200 kg |
| Propylene glycol | 0.150 kg |
| Gelatin (succinylated) | 0.050 kg |
| Standard sodium Phosphate buffer to pH 7 | 0.073 kg |
| Purified water to | 2.000 kg |

A slow release sublingual β-1,3-glucan tablet of this example was prepared according to the process of the invention as follows:

1. Huttlin Turbojet sterilised using heat (180° C.) as instructed by the equipment manufacturer.
2. Hydrogel core material loaded into the Huttlin Turbojet chamber by vacuum, fluidized and heated up to 60° C. for one hour.
3. Hydrogel core temperature to reduced to 40° C.
4. Content of chamber fluidized at a rate of 300 cubic meters per hour.
5. β-1,3-glucan coating turbojet coated onto the hydrogel core under saturated moisture conditions at 25 g/minute.
6. Resultant product dried to less than 3% moisture content.
7. Each 200 mg microcapsule contains 10 mg of β-1,3-glucan.
8. Product compressed into 200 mg tablets according to standard procedures used in the art.
9. Product packed in nitrogen flushed aluminium/aluminium foil pack and stored at a temperature not exceeding 25° C.

The tablets of this example have a slow dissolution rate (less than minutes) due to the presence of a high percentage of gelatin, polyvinylpyrrolidone (Povidone) and albumin in the hydrogel core. This combination is ideal for slow release products which allow the active material to have continuous contact with the target absorption site, such as the oral mucosal membrane.

The recommended dosage regime for a product according to this example, where it is used for the treatment or alleviation of an allergic condition, is: one tablet dissolved under the tongue daily, for four weeks prior to spring and continue for six months thereafter. It is recommended that no food or drink be taken fifteen minutes before or after medication.

A product according to this example was trialed by a 49 year old female (Mrs Y) and a 39 year old male (Mr X) both of whom suffered severe hay fever for many years. It was determined using skin sensitivity tests that both subjects suffered from allergic reactions to rye grass, pollen and house dust.

After taking the tablets of the present example in the dose recommended above, both subjects reported that the incidence of sneezing, itchy eyes and runny nose were minimal this spring season, compared to previous years. Both subjects requested that they be able to repeat the treatment in the following year to determine whether their symptoms may be completely cured.

While not wishing to be bound to any particular theory, the inventors of the present invention believe the sublingual use of β-1,3-glucan probably desensitised the immune system so that the inflammatory response was down regulated.

The β-1,3-glucan sublingual tablet of the present example was also given to one severe asthmatic male aged 40 (Mr Z) who has to use bronchodilator spray and corticosteroid medication consistently. After two weeks of using the medication (one tablet per day, dissolved under the tongue), the wheezing incidence was greatly reduced and the frequency of the need to use the bronchodilator spray and corticosteroid medication was halved. However, while the medication was useful to reduce his asthmatic conditions, for some unknown reasons, there were incidences of nose bleeding. The β-1,3-glucan medication was stopped accordingly.

Example 4

Stabilization of Biologically Active Proteins

As previously mentioned herein biological proteins and peptides have wide application in a number of industries, including the pharmaceutical industry. However, many of these proteins may be unstable at storage temperatures, such as room temperature.

The efficacy of the present invention in producing a stable protein product is demonstrated in this example using Interferon however, it will be appreciated that it is equally applicable to the preparation of other proteins or peptides.

Interferon α, β and γ are antiviral, antitumour and immunity modulating proteins. The method commonly used to introduce exogenous interferon into the body of an animal is by injection. Natural and recombinant interferon α 2a and 2b are commercially available as 3 million to 10 million IU injections for treatment of viral and tumour diseases. All commercial interferon injection products require storage at approximately 4° C. to 8° C. because they are unstable at elevated temperatures.

Administration of interferon by injection, at 3 million to 5 million IU dosages, are associated with significant side effects. In addition, as interferon is not a native blood protein, it is quite common that a patient may mount an immune response thereto, after a few injections. Accordingly, subsequent dosages need to be significantly increased in order for the interferon to have effect. This in turn may worsen the side effects. Further, when administered by injection, exogenous interferon will be carried via the blood to the liver and quickly metabolised.

Example 4a

Stabilized Interferon α 3 Million IU Injection

The present example provides an interferon injection which is stable at room temperature.

The stabilized interferon injection formulation comprises the following components:

|  | 4 kg Batch |
| --- | --- |
| Hydrogel core |  |
| Gelatin | 3.208 kg |
| Polyvinylpyrrolidone (Povidone) | 0.400 kg |
| Coating Liquid |  |
| Interferon α 2b 40 billion IU |  |
| Mannitol | 0.200 kg |
| Propylene glycol | 0.075 kg |
| Gelatin (succinylated) | 0.025 kg |
| Glycine | 0.012 kg |
| Egg Albumin | 0.001 kg |
| Standard sodium phosphate buffers to pH 7 | 0.073 kg |
| Water for injection to | 2.000 kg |

It will be appreciated that the term "water for injection" is one standard in the art. It refers to a standard grade of water suitable for use in formulating injectable compositions, as described in standard pharmacopoeia.

The stabilized interferon injection of the present example was prepared according to the invention using the following steps:

1 Inferon α, glycine, mannitol, gelatin succinylated, propylene glycol, and buffers are dissolved in water for injection then filtered through 0.22 micron membrane filter. Albumin was added and made up to weight with water for injection.
2 Huttlin Turbojet chamber sterilised using heat (180° C.) as instructed by the equipment manufacturer.
3 The Huttlin apparatus was switched to circulating filtered nitrogen mode.
4 Hydrogel core material loaded into the Huttlin Turbojet chamber by vacuum, fluidized and heated up to 60° C. for one hour.
5 Hydrogel core product temperature reduced to 40° C.
6 Content of chamber fluidized at a rate of 300 cubic meters per hour.
7 Interferon α coating turbojet sprayed onto the hydrogel core under saturated moisture conditions at a rate of 25 g/minute.
8 Resultant product dried to less than 2% moisture content.
9 Product packaged in nitrogen flushed injection vials under aseptic fill conditions.

Each 50 mg of the microcapsules prepared according to the present example contains 3 million IU interferon α.

Example 4b

Stabilized Interferon α 60,000 IU Pessaries

Room temperature stabilized Interferon pessaries can be made to prevent and treat papilloma infections and other viral diseases in the vaginal surface.

The stabilized interferon pessaries formulation of the present example comprised the following components:

|  | 4 kg Batch |
|---|---|
| Hydrogel core | |
| Polyvinylpyrrolidone (Povidone)/Acetic acid ethenyl polymer | 3.508 kg |
| Coating Liquid | |
| Interferon α 2b 40 billion IU | |
| Mannitol | 0.200 kg |
| Propylene glycol | 0.150 kg |
| Gelatin (succinylated) | 0.050 kg |
| Glycine | 0.012 kg |
| Egg Albumin | 0.001 kg |
| Standard sodium phosphate buffers to pH 7 | 0.073 kg |
| Water for injection to | 2.000 kg |

The stabilized interferon pessaries of the present example were prepared according to the invention using the following steps:

1. Interferon α, glycine, mannitol, gelatin succinylated, propylene glycol, and buffers were dissolved in water then filtered through 0.22 micron membrane filter. Albumin was added and made up to weight with water for injection.
2. Huttlin Turbojet heat sterilized at 180° C. as instructed by the equipment manufacture.
3. Apparatus switched to circulating filtered nitrogen mode.
4. Hydrogel core material loaded into the Huttlin Turbojet chamber by vacuum, fluidized and heated up to 60° C. for one hour.
5. Hydrogel core product temperature reduced to 40° C.
6. Contents of the chamber fluidized at a rate of 300 cubic meters per hour.
9. Interferon α coating turbojet sprayed onto the hydrogel core under saturated moisture conditions at a rate of 25 g/minute.
8. Resultant product dried to less than 2% moisture content.
9 Product compressed into 1 g pessaries, according to standard procedures.
10 Product packaged in nitrogen flushed aluminium/aluminium foil packs and stored at a temperature not exceeding 25° C.

Each 1 g microcapsule prepared according to this example contains 60,000 IU interferon α.

Example 4c

Stabilized Interferon A 2000 IU & Muramidase Sublingual Tablet

Interferon α at ultra low dose (less than 10,000 IU/dose/adult) has been demonstrated to be an effective medication in treatment of viral and tumour diseases.

Subcutaneously administered interferon α is now considered to be the standard therapy for the management of hepatitis B and C and there are a number of commercially available products therefor; for example, Wellferon ™ Injection (Glaxo Wellcome), Intron-ATM Injection (Schering Plough), Roferon ATM Injection (Hoffmann-La Roche) and Anferon (Hualida Tianjin, China). However, a number of disadvantages may be associated with the use of such products including, for example: self-administration by patients is painful and requires training; high-doses may be associated with a number of side effects including vomiting, nausea, dizziness, nasal discharge and other flu like symptoms; the cost of treatment may be considered high, for example a normal course of treatment for hepatitis B & C with Roferon A Injection would cost around AU$8000 in Australia; and the products are not stable at room temperature and must be stored under refrigeration.

Studies conducted over approximately the past ten years have indicated that low doses of interferon α may be administered via the oromucosal route (including sublingual administration) with efficacy.

The present example provides a dosage form which may be administered via the oromucosal route (buccal or sublingual).

The sublingual slow release formulation of the present invention contains both interferon α (2000 IU) and muramidase hydrochloride (50 mg) and is useful in the treatment or amelioration of chronic viral diseases; muramidase hydrochloride is an antiviral agent with a history of extensive use in Asian countries.

The stabilized interferon α and muramidase sublingual tablet formulation of the present example comprised the following components:

| | 4 kg Batch |
|---|---|
| Hydrogel core | |
| Gelatin | 1.480 k |
| Polyvinylpyrrolidone (Povidone) | 0.400 kg |
| Muramidase Hydrochloride | 1.000 kg |
| Coating Liquid | |
| Interferon α 2b 40 billion IU | |
| Mannitol | 0.200 kg |
| Propylene glycol | 0.150 kg |
| Gelatin (succinylated) | 0.500 kg |
| Glycine | 0.120 kg |
| Egg Albumin | 0.020 kg |
| Ascorbic Acid | 0.057 kg |
| Standard sodium phosphate buffers to pH 7 | 0.073 kg |
| Water for injection to | 4.000 kg |

The stabilized interferon α and muramidase sublingual tablets of the present example were prepared according to the invention using the following steps:

1 interferon α, glycine, mannitol, gelatin succinylated, propylene glycol, ascorbic acid and buffers were dissolved in water for injection then albumin was added and made up to weight with water for injection.
2 Huttlin Turbojet chamber sterilised by heating at 180° C. as instructed by the equipment manufacturer.
3 Apparatus switched to circulating filtered nitrogen mode.
4 Hydrogel core material loaded into the modified Huttlin Turbojet chamber via vacuum, fluidized and heated up to 60° C. for one hour.
5 Hydrogel core product temperature reduced to 40° C.
6 Content of apparatus chamber fluidized at a rate of 300 cubic meters per hour.
7 Interferon α coating turbojet sprayed onto the hydrogel core under saturated moisture conditions at a rate of 25 g/minute.
8 Resultant product dried to less than 2% moisture content.
9 Microcapsules compressed, according to standard procedures used in the art, into 200 mg tablets and packed in nitrogen flushed aluminium/aluminium foil packs and stored at a temperature not exceeding 25° C.

Each 200 mg tablet produced according to this example contains 2,000 IU interferon α 2b and 50 mg of muramidase hydrochloride, has a slow dissolution profile and requires not less than ten minutes to dissolve in the mouth. It is designed as a slow release sublingual product.

A product according to the present example is recommended to be administered for the prevention and/or treatment of chronic viral infections, according to the following preferable dosage regime: one tablet every two days dissolved under the tongue over six months to one year.

The stability of the actives (interferon α 2b and muramidase) within the tablets of three different batches of the product produced according to this example was studied at three different temperatures. The results are collected in Table 9 below.

The potency of each active was assessed according to standard procedures used in the art. Briefly, the following steps were taken:
1 The interferon and muramidase were extracted from the existing solid phase into a stable and buffered liquid medium.
2 The liquid extracted was subjected to a Cytopathic Effect Assay (CPE) to determine the antiviral activity of interferon in the tablet (according to the current method of British/European Pharmacopoeia 2000).
3 The liquid extract was subjected to HPLC analysis to determine the quantity of muramidase in the tablets.

liquid form, with a viable commercial shelf life (of approximately twelve to eighteen months for example) are unavailable.

A viable alternative is to have the principal active ingredient (interferon α) presented as a pre-constituted room temperature stable tablet. Accordingly, just prior to use the interferon α tablet may be added to a nasal spray bottle containing an acceptable liquid diluent. The reconstituted solution would have a shelf life of around four weeks at room temperature; which shelf life would be suitable for the length of treatment of most respiratory infections. The user may discard the bottle at the completion of treatment.

Accordingly, the present example presents a consumer product containing two components:
1 A foiled packed interferon tablet containing 50,000 IU of stabilized interferon α; prepared according to the process of the invention; and
2 A bottle containing 5 ml of an acceptable diluent, and having a screw on nasal spray applicator.

It is preferred that the nasal spray applicator sprays a metered dose of 0.1 ml of solution. According to the present example, at this dosage rate, 1000 IU interferon α would be administered with each spray.

TABLE 9

| 4° C. | IFN + Mu Bx 1 IFN α 2b IU | IFN + Mu Bx 2 IFN α 2b IU | IFN + Mu Bx 3 IFN α 2b IU | 4° C. | IFN +Mu Bx 1 Muramidase HCl mg | IFN +Mu Bx 2 Muramidase HCl mg | IFN + Mu Bx 3 Muramidase HCl mg |
|---|---|---|---|---|---|---|---|
| zero time | 2200 | 1800 | 2200 | zero time | 47.5 | 50.0 | 47.5 |
| 3 months | 2400 | 2200 | 2200 | 3 months | 47.5 | 50.0 | 47.5 |
| 6 months | 1400 | 3200 | 3000 | 6 months | 48.0 | 48.5 | 46.0 |
| 9 months | 2000 | 2400 | 1800 | 9 months | 48.0 | 49.0 | 47.5 |
| 12 months | 3000 | 1600 | 3550 | 12 months | 46.5 | 49.0 | 49.0 |
| 24 months | 2400 | 2200 | 2400 | 24 months | 47.0 | 48.5 | 47.5 |
| 25° C. | IFN α 2b | IFN α 2b | IFN α 2b | 25° C. | Muramidase HCl | Muramidase HCl | Muramidase HCl |
| zero time | 2200 | 1800 | 2200 | zero time | 47.5 | 50.0 | 47.5 |
| 3 months | 2800 | 2200 | 2400 | 3 months | 47.5 | 50.0 | 47.5 |
| 6 months | 1000 | 1400 | 2850 | 6 months | 48.0 | 49.0 | 48.0 |
| 9 months | 1600 | 2200 | 1800 | 9 months | 48.0 | 49.5 | 48.5 |
| 12 months | 2200 | 1850 | 2000 | 12 months | 49.0 | 46.5 | 48.5 |
| 24 months | 2400 | 2200 | 2200 | 24 months | 48.0 | 47.5 | 48.0 |
| 35° C. | IFN α 2b | IFN α 2b | IFN α 2b | 35° C. | Muramidase HCl | Muramidase HCl | Muramidase HCl |
| zero time | 2200 | 1800 | 2200 | zero time | 47.5 | 50.0 | 47.5 |
| 3 months | 2400 | 2200 | 2000 | 3 months | 47.5 | 50.0 | 47.5 |
| 6 months | 2800 | 2000 | 2200 | 6 months | 48.5 | 48.5 | 48.0 |
| 9 months | 2000 | 1600 | 3800 | 9 months | 48.0 | 48.5 | 47.5 |
| 12 months | 2400 | 1800 | 3000 | 12 months | 48.5 | 48.5 | 48.0 |
| 24 months | 2000 | 2400 | 2000 | 24 months | 48.0 | 48.5 | 48.0 |

Example 4d

Stabilized Interferon α Nasal Spray for Prevention of Cold, Flu and Other Respiratory Diseases Interferon α is known to be effective against viral respiratory diseases. Clinical studies in animals, including humans, have demonstrated interferon α nasal spray at a dose around a few hundred units to over one million units is effective against respiratory infections, including those associated with the flu and colds. However, at high dosages nose bleeding and flu-like symptoms may be observed.

Correctly formulated interferon α 2b in aqueous phase can be stable up to one month, but not more than two months, at room temperature according to the information supplied by manufacturers of interferon α 2b. Accordingly, interferon nasal sprays for the treatment and/or prevention of colds, the flu and other respiratory diseases, in a ready to use A formulation according to the present example is preferably administered at a rate of one 0.1 ml (1000 IU) spray per nostril daily starting just prior to cold and flu season.

The stabilized tablets of the present example comprise the following components:

|  | 4 kg Batch |
|---|---|
| Hydrogel core | |
| Polyvinylpyrrolidone (Povidone)/Acetic acid ethenyl polymer | 3.508 kg |
| Coating Liquid | |
| Interferon α 2b 40 billion IU | |
| Mannitol | 0.200 kg |

-continued

|  | 4 kg Batch |
| --- | --- |
| Propylene glycol | 0.150 kg |
| Gelatin (succinylated) | 0.050 kg |
| Glycine | 0.012 kg |
| Egg Albumin | 0.001 kg |
| Standard sodium phosphate buffer to pH 7 | 0.073 kg |
| Water for injection to | 2.000 kg |

The stabilized tablets of the present example were prepared according to the invention using the following steps:
1. Interferon α, glycine, mannitol, gelatin succinylated, propylene glycol, and buffers are dissolves in water for injection then filtered through 0.22 micron membrane filter. Add albumin and make up to weight with water for injection.
2. Huttlin Turbojet chamber sterilized by heat treatment at 180° C. as instructed by the equipment manufacture.
3. Apparatus switched to circulating filtered nitrogen mode.
4. Hydrogel material core loaded into the Huttlin Turbojet chamber via vacuum, fluidized and heated up to 60° C. for one hour.
5. Hydrogel core product temperature reduced to 40° C.
6. Contents of the apparatus chamber fluidized at a rate of 300 cubic meters per hour.
7. Interferon α coating turbojet sprayed onto the hydrogel core under saturated moisture conditions at a rate of 25 g/minute.
8 Resultant product dried to less than 2% moisture content.
9 Microcapsules compressed, according to standard procedures in the art, into 200 mg tablets.
10 Tablets packaged into nitrogen flushed aluminium/aluminium foil packs and stored at a temperature not exceeding 25° C.

Each 200 mg tablets produced according to this example contains 50,000 IU interferon α.

The constituents of the liquid diluent formulation of the present example are provided in Table 10 below.

TABLE 10

| | % w/w |
|---|---|
| Gelatin BP/Eur.P | 0.10 |
| Povidone BP/Eur.P | 0.10 |
| Disodium edetate BP/Eur.P | 0.14 |
| Polysorbate 80 BP/Eur.P | 0.20 |
| Dextran 45,000 BP/Eur.P | 0.22 |
| Sodium dihydrogen phosphate BP/Eur.P (Anhydrous Weight) | 0.27 |
| Disodium hydrogen phosphate BP/Eur.P (Anhydrous Weight) | 0.58 |
| Glycine BP/Eur.P | 0.10 |
| Sodium propyl hydroxybenzoate BP/Eur.P | 0.03 |
| Sodium methyl hydroxybenzoate BP/Eur.P | 0.09 |
| Albumin BPC | 0.05 |
| TOTAL | 2.93 |
| Purified water BP/Eur.P to | 100% |

Example 4e

Stabilized Interferon α Nasal Spray for Treatment of Cold, Flu and Other Respiratory Diseases The present example, provides an alternative diluent formulation containing additional active ingredients that may help relieve cold and flu symptoms.

The consumer product of the present example contains the two components listed in Example 4d; the tablet containing the interferon α and the diluent within a spray applicator bottle or the like. Similarly, the reconstituted interferon nasal spray will contain 1000 IU interferon α/0.1 ml.

The preferred dosage regime of the present example is: one 0.1 ml (1000 IU) spray per nostril morning and night when mild flu or cold symptoms appears. Continue treatment for five to ten days.

The tablet component of the present example is prepared according to process of Example 4d.

The diluent formula of the present formulation is given in Table 11 below:

TABLE 11

| | % w/w |
|---|---|
| Oxymetazoline hydrochloride USP | 0.05 |
| Dexchlorpheniramine meleate USP | 1.00 |
| Gelatin BP/Eur.P | 0.10 |
| Povidone BP/Eur.P | 0.10 |
| Disodium edetate BP/Eur.P | 0.14 |
| Polysorbate 80 BP/Eur.P | 0.20 |
| Dextran 45,000 BP/Eur.P | 0.22 |
| Sodium dihydrogen phosphate BP/Eur.P (Anhydrous Weight) | 0.27 |
| Disodium hydrogen phosphate BP/Eur.P (Anhydrous Weight) | 0.58 |
| Glycine BP/Eur.P | 0.10 |
| Sodium propyl hydroxybenzoate BP/Eur.P | 0.03 |
| Sodium methyl hydroxybenzoate BP/Eur.P | 0.09 |
| Albumin BPC | 0.05 |
| TOTAL | 2.93 |
| Purified water BP/Eur.P to | 100% |

Example 4f

Stabilized Interferon α Eye Wash or Drops for Prevention of Red Eye Disease

As previously discussed, correctly formulated aqueous interferon α may be stable up to one month, but not two, at room temperature. Accordingly, interferon eye washes or drops, in a ready to use liquid form, with a viable commercial shelf life (of approximately twelve to eighteen months, for example) are unavailable.

A viable alternative is to have the principal active ingredient (interferon α) presented as a preconstituted room temperature stable tablet. Accordingly, just prior to use the interferon α tablet may be added to an eye wash, or eye drop, bottle containing an acceptable liquid diluent. The reconstituted solution would have a shelf life of around four weeks at room temperature. The user may discard the bottle at the completion of treatment.

The consumer product of the present example contains the two components listed in Example 4d; the tablet containing the interferon α and the diluent (albeit in an appropriate eye wash or drop bottle, in this example). Similarly, the reconstituted interferon eye wash or drops contain 1000 IU interferon α/0.1 ml, with 0.1 ml being the preferred single administration dose.

The preferred dosage regime of this example is: one 0.1 ml (1000 IU) spray/drop per eye, twice daily for treatment of red eye.

The interferon α tablet formulae of the present example is formulated and processed according to that described in Example 4d above.

The diluent formulation of the present example is provided in Table 12 below. It will be appreciated that this liquid diluent is preferably autoclaved, or otherwise sterilised.

TABLE 12

|  | % w/w |
|---|---|
| Povidone BP/Eur.P | 0.10 |
| Disodium edetate BP/Eur.P | 0.14 |
| Polysorbate 80 BP/Eur.P | 0.20 |
| Dextran 45,000 BP/Eur.P | 0.22 |
| Sodium dihydrogen phosphate BP/Eur.P (Anhydrous Weight) | 0.27 |
| Disodium hydrogen phosphate BP/Eur.P (Anhydrous Weight) | 0.58 |
| Glycine BP/Eur.P | 0.10 |
| Sodium propyl hydroxybenzoate BP/Eur.P | 0.03 |
| Sodium methyl hydroxybenzoate BP/Eur.P | 0.09 |
| Albumin BPC | 0.05 |
| TOTAL | 1.78 |
| Purified water BP/Eur.P to | 100% |

Example 4g

Stabilized Interferon Skin Spray—Same Formulation as Eyewash

A skin spray, for wound healing, for example, was formulated according to

Example 4f. However, in this example, the liquid diluent was presented in an appropriate container for delivery to the skin.

Example 4h

Stabilized Erythropoietin (EPO) for Sublingual Delivery

Stabilized formulations of EPO were prepared in tablet form according to the following process.

|  | % w/w |
|---|---|
| Hydrogel Core |  |
| Dextrose (anhydrous) BP | 46.52 |
| Starch BP (anhydrous wt) | 20.00 |
| Gelatin BP/Eur.P anhydrous wt | 20.00 |
| Carmellose BP anhydrous wt | 2.00 |
| Coating Liquid |  |
| EPO (Epoetin Alfa) 250,00 IU |  |
| Dextran 40,000 BP/Eur.P | 0.600 |
| Sodium Dihydrogen Phosphate BP /Eur.P | 0.042 |
| Disodium Hydrogen Phosphate BP/Eur.P (anhydrous wt) | 0.057 |
| Glycine BP/Eur.P | 0.030 |
| Trehalose | 0.600 |
| Sodium Edetate BP | 0.025 |
| Propylene Glycol BP | 0.050 |
| Egg Albumin | 5.030 |
| Sodium Chloride BP | 0.046 |
| Leucine USP | 3.000 |
| TOTAL | 98% |
| Purified Water BP/Eur.P to | 100% |

The sublingual EPO tablets of the present example were prepared according to the invention using the following steps:
1 EPO, dextran, glycine, trehalose, sodium edetate, propylene glycol, sodium chloride, leucine and buffers were dissolved in purified water then albumin was added and made up to weight with purified water.

2 Huttlin Turbojet heat sterilised at 180° C. as instructed by the equipment manufacturer.
3 Apparatus switched to circulating filtered nitrogen mode.
4 Hydrogel core material loaded into the modified Huttlin Turbojet chamber via vacuum, fluidized and heated up to 60° C. for one hour.
5 Hydrogel core product temperature reduced to 40° C.
6 Contents of the chamber fluidized at a rate of 300 cubic meters per hour.
7 EPO coating turbojet sprayed onto the hydrogel core under saturated moisture conditions at a rate of 25 g/minute.

8 Resultant product dried to less than 2% moisture content.

9 Product compressed into 200 mg tablets according to standard procedures.

An animal study was conducted using the formulations so produced. Rats were divided into four groups. Group 1 received 50 IU EPO via subcutaneous injection on day one, and blood samples were taken for analysis on days two, four and six for reticulocyte determination. This mode of administration mimics the current delivery route for EPO therapy.

In Group 2, rats received a daily dose of 125 IU EPO via sublingual delivery with the formulation of this example on days one, two and three. Blood samples were taken on days two, four, six and eight for reticulocyte determination.

The Group 3 rats received a daily dose of 125 IU EPO via sublingual delivery on days one, two, three, four and five. Blood samples were taken on days two, four, six, eight and ten for reticulocyte determination.

Controlled rats received either a subcutaneous injection of saline of the same volume as the 50 IU EPO subcutaneous injection for Group 1. Control Group 2 received a formulation according to this example containing no EPO.

Results

The results are shown graphically in FIG. 1, with control animals being represented in the "normal range" figures presentation. Rats received sublingual EPO showed demonstrably elevated reticulocyte counts above the normal range for control animals, indicating that the EPO delivered sublingually was active.

The subcutaneously injected EPO showed peak reticulocyte counts after two days, which rapidly fell off to the normal range at four days.

The formulation of this example was tested for stability, and results are shown in FIG. 2. As shown in this figure, the EPO containing sublingual tablet is stable at room temperature for at least nine months. The activity of EPO was determined by human EPO immunoassay and found to be fully biologically active, as measured by reticulocyte counts in rats.

This example shows that stabilized proteins, such as erythropoietin, are released and absorbed through contact with mucosal surface of the body, including sublingual delivery, nasal delivery and vaginal delivery. These mucosal areas are rich in lymphoidal tissue which allows transport of the proteins into the body for treatment of anemia caused by, for example, kidney failure, AIDS, cancer, genetic diseases, operation and menstruation.

Those skilled in the art will appreciate that the invention described herein is susceptible to variations and modifications other than those specifically described. It is to be understood that the invention includes all such variations and modifications. The invention also includes all of the steps, features, and compositions referred to or indicated in this specification, individually or collectively, and any and all combinations of any two or more of said steps or features.

Particularly, it will be appreciated by those of general skill in the art to which the present invention relates, that while the present invention has been described and exemplified with reference to the preparation of specific proteins and micro-organisms it is equally applicable to the preparation of any cells and/or proteins or peptides of interest. For example, the process of the invention may be readily applicable to the preparation of hormones, cytokines, and growth factors such as human or animal growth hormone, or derivatives thereof; erythropoietin (EPO) including those produced by recombinant techniques for example Epoetin α, Epoetin β, and Epoetin γ; calcitonin; interferons including α- and β- and γ-interferons; interleukins such as IL 2; insulins; colony stimulating factors such as G-CSF and GM-CSF. Examples of enzymes which may be used in the invention include streptokinase, muramidase, pancreas, amylase, protease, lypase, cellulase, bromelain, papain and the like. The formulations may include two or more different enzymes.

The specification provides examples of preferred dosage rates for the use of a number of the novel formulations made according to the invention. Alternative dosages and concentrations of active therein are envisaged by the inventors and those of general skill in the art to which the invention relates will readily be able to formulate products, according to the present invention, which have alternative concentrations of active therein.

Biological proteins being stabilized as microcapsules in this invention are also able to be released when in contact with mucosal surfaces of the body eg sublingual, nasal, vaginal. These mucosal areas are rich in lymphoidal tissue which allow transport of the protein into the body. Investigations of various proteins as subcutaneous injections by Charman et al (*J. Pharm. Sci.*, Vol 89, pages 168–177 (2000)) and later by McLennan (APSA 2001 *Conference Proceedings*), showed lymphatic absorption of proteins increased with molecular weight of the protein and the lymphatic system was significant in contributing to the overall systemic availability of proteins administered via subcutaneous injections. The stabilised protein microcapsules can allow more patient acceptable dosage forms, such as a sublingual tablet, nasal spray or vaginal pessary, than subcutaneous injection.

Further, it will be appreciated that a product according to the invention may be manipulated or further formulated in order to arrive at a desired dose form. For example, the microcapsules of the invention may be encapsulated to form standard capsule unit doses, or may be combined with various standard excipients and diluents used in the art, to form tablets or liquid formulations, for example. Those of skill in the art will appreciate many other ways in which the micro-capsules of the invention may be further formulated and that they are contemplated by the inventors of the present invention.

Finally, it is contemplated by the inventors of the present invention that the novel process described herein may be used to prepare other materials and to manipulate materials to particular ends. In particular, it is envisaged that the inventive process may be manipulated to allow for enteric coating of microcapsules using solvents or aqueous methods such as sodium salts of cellulose acetate phthalate, to create sustained release properties by changing the core material polymers to a higher molecular weight or by using a combination of hydrogel core such as high molecular weight gelatin, polyvinyl pyrrolidone, alginates, carboxymethyl cellulose, various cellulose derivative, polyethylene glycols, albumin, dextran, carrageenan (one of ordinary skill in the art of formulation will be able to provide various combinations to create a desired release profile), create time release properties by varying the nature of polymers used and the thickness of the coatings and to allow for microdistribution of trace materials among large amount of solid mass.

Titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the field of endeavour.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

What is claimed is:

1. A composition comprising microparticle cores coated with a coating layer comprising a biologically active material and a sugar polymer, wherein the resulting microparticles comprise water-soluble gel forming solid particles selected from two or more of the group consisting of dextrose, starch, gelatin, albumin and polyvinyl pyrrolidone.

2. The composition according to claim 1, wherein the resulting coated microparticles are coated with an enteric coating, a film coating, a moisture repellent coating, a taste-masking coating, or a combination of any such coatings.

3. The composition of claim 1, wherein the biologically active material is selected from the group consisting of a protein, a peptide and a cell.

4. The composition of claim 1, wherein the biologically active material is selected from the group consisting of a hormone, a cytokine, a growth hormone, and a combination of any two or more thereof.

5. The composition of claim 1, wherein the biologically active material is selected from the group consisting of a human or animal growth hormone, erythropoietin, calcitonin, interferon, interleukin, insulin, and colony stimulating factor.

6. The composition of claim 1, wherein the biologically active material is a microorganism.

7. The composition of claim 6, wherein said microorganism is *Bifidus* or *Lactobacilli*.

8. The composition of claim 1, wherein the biologically active material is an anti-diarrhea agent.

9. The composition of claim 1, wherein the biologically active material is a growth promotant.

10. The composition of claim 1, wherein said microparticles comprise a member selected from the group consisting of an acrylate, acrylate derivative, albumin, alginate, carbomer, carrageenan, cellulose, cellulose derivatives, dextran, dextrin, gelatine, polyvinylpyrrolidone, and starch.

11. The composition of claim 1, wherein said composition is in the form of an injectable composition, sublingual tablet, oral tablet, sustained release sublingual tablet, microcapsule, pessaries, preconstituted solid dose for nasal spray or drops, aqueous drops, eye wash or drops, skin washing solutions, or a feed premix.

* * * * *